(12) United States Patent
Kuechler et al.

(10) Patent No.: US 7,279,012 B2
(45) Date of Patent: Oct. 9, 2007

(54) PROCESS FOR PRODUCING OLEFINS

(75) Inventors: Keith H. Kuechler, Friendswood, TX (US); Jeffrey L. Brinen, League City, TX (US); Philip Andrew Ruziska, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 679 days.

(21) Appl. No.: 10/882,722

(22) Filed: Jul. 1, 2004

(65) Prior Publication Data

US 2006/0004239 A1 Jan. 5, 2006

(51) Int. Cl.
*C07C 7/00* (2006.01)

(52) U.S. Cl. .................. 858/809; 585/802; 585/639; 585/638

(58) Field of Classification Search .............. None
See application file for complete search history.

(56) References Cited

U.S. PATENT DOCUMENTS

| 6,121,504 | A  | 9/2000  | Kuechler et al. ........... 585/640 |
|---|---|---|---|
| 6,303,841 | B1 | 10/2001 | Senetar et al. ............. 585/639 |
| 6,403,854 | B1 | 6/2002  | Miller et al. ............... 585/638 |
| 6,459,009 | B1 | 10/2002 | Miller et al. ............... 585/809 |
| 2002/0007101 | A1 | 1/2002 | Senetar et al. ............ 585/809 |
| 2003/0130555 | A1 | 7/2003 | Cheng et al. .............. 585/804 |

*Primary Examiner*—Tam M. Nguyen

(57) ABSTRACT

A process for producing olefins comprises providing a vapor product stream from an oxygenate to olefin reaction, the vapor product stream comprising $C_2$ to $C_4$ olefins, $C_2$ to $C_6$ carbonyl compounds and water. The vapor product stream is cooled to provide a first vapor effluent stream comprising no more than 10 wt. % water, and a liquid water-rich stream. The first vapor effluent stream, and a first wash flash vapor stream, are compressed from a first pressure to a second pressure greater than said first pressure to form a second vapor effluent stream, which is then cooled to form a cooled second effluent stream that is at least partially in the vapor state. At least part of the cooled second effluent stream is washed with a liquid alcohol-containing stream, at a third pressure greater than the first pressure but not greater than the second pressure, to produce a wash liquid stream, which comprises $C_3$ and $C_4$ olefins, and a wash vapor stream, which contains less $C_2$ to $C_6$ carbonyl compounds than the first vapor effluent stream. The wash liquid stream is exposed to a pressure of at least the first pressure but less than the third pressure to form a first wash flash liquid stream and the first wash flash vapor stream, the first wash flash vapor stream being provided for compression with the first vapor effluent stream.

97 Claims, 3 Drawing Sheets

PROCESS FOR PRODUCING OLEFINS

FIELD

The present invention relates to a process for producing olefins and, in particular, ethylene and/or propylene.

BACKGROUND

Olefins are traditionally produced from petroleum feedstocks by catalytic or steam cracking processes. These cracking processes, especially steam cracking, produce light olefin(s), such as ethylene and/or propylene, from a variety of hydrocarbon feedstock. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids or carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Other known syngas production processes include conventional steam reforming, autothermal reforming, or a combination thereof.

The preferred process for converting an oxygenate, such as methanol, into one or more olefin(s), primarily ethylene and/or propylene, involves contacting the feedstock with a catalyst composition, typically containing a molecular sieve catalyst. The effluent produced by such a process is a complex mixture comprising the desired light olefins, unconverted oxygenates, by-product oxygenates, heavier hydrocarbons and large amounts of water. The separation and purification of this mixture to recover the light olefins and other valuable by-products is critical to the overall efficiency and cost effectiveness of the process. In particular, it is important that the purification scheme produces products that are substantially free of impurities, which could adversely effect downstream processing.

For example, certain oxygenate components present in the effluent from an oxygenate conversion process, particularly aldehydes and ketones, may cause problems in olefin recovery operations and in derivative manufacturing processes that feed and react $C_4+$ hydrocarbons. There is therefore a need to ensure that the effluent purification scheme effectively removes aldehydes and ketones from the olefinic and $C_4+$ hydrocarbon components while at the same time minimizing loss of useful product.

U.S. Pat. No. 6,303,841 and U.S. patent application Publication No. 2002/0007101, published Jan. 17, 2002, disclose a process for producing ethylene from oxygenates in which the oxygenate conversion effluent stream is compressed in a multi-stage compressor to a pressure of 1050 to 2860 kPa (150 to 400 psia), preferably 1750 to 2450 kPa (250 to 350 psia), washed with methanol and then water to remove unreacted oxygenates and then contacted with caustic to remove carbon dioxide. The carbon dioxide depleted stream is dried with a solid desiccant and passed to a deethanizer zone to provide a light hydrocarbon feedstream comprising hydrogen, methane, ethylene and ethane, and a deethanized stream comprising propylene, propane, and $C_4+$ olefins. The light hydrocarbon stream is passed to a demethanizer zone operating at a temperature greater than 45° C. to provide a bottom stream comprising ethylene and ethane and an overhead stream comprising hydrogen, methane, and ethylene. The bottom stream is fed to a $C_2$ splitter zone to produce the ethylene product stream and an ethane stream, whereas the overhead stream is fed to a pressure swing adsorption zone to remove hydrogen and methane and produce an ethylene-containing stream which is combined with the oxygenate conversion effluent stream.

U.S. Pat. Nos. 6,403,854 and 6,459,009 to Miller et al. disclose a process for converting oxygenate to light olefins in which the reactor effluent is quenched with an aqueous stream in a two-stage process to facilitate the separation of hydrocarbon gases from any entrained catalyst fines, as well as to remove water and any heavy by-products such as $C_6+$ hydrocarbons. A portion of the waste water stream withdrawn from the bottom of the quench tower is recycled to the quench tower at a point above where the reactor effluent is introduced to the quench tower. The vapor product stream from the quench tower is compressed, passed to an adsorption zone for the selective removal of oxygenates and then passed to a caustic wash zone for removal of carbon dioxide. The resultant carbon dioxide free light olefin stream is passed to a dryer zone for the removal of water and passed to a conventional light olefin recovery zone.

U.S. patent application Publication No. 2003/0130555, published Jul. 10, 2003, discloses a process for separating oxygenated hydrocarbons from the olefin product of an oxygenate to conversion olefins reaction. The product is initially sent to a cooling unit, such as a quench tower, from which cooled olefin product is separated as an olefin vapor stream. The water containing bottoms stream can be recycled through a heat exchanger for cooling and/or removed from the cooling unit to a first separator, such as a distillation column, to provide an oxygenated hydrocarbon product of reduced water content and remaining water as a bottoms product. The olefin vapor stream is compressed to at least 30 psia (207 kPa), preferably 100 to 500 psia (689 to 3447 kPa), and directed to a second separator that provides an olefin vapor product and a liquid oxygenated hydrocarbon-containing stream. The liquid oxygenated hydrocarbon containing stream can then be combined with the water containing bottoms stream or directly added to the first separator to provide an oxygenated hydrocarbon product recovered from the first separator that is reduced in water content and can be used as fuel or co-feed for the oxygenate reaction process. Before or after the compression step, the olefin vapor can be washed with methanol and/or water at a temperature of 40 to 200° F. (4 to 93° C.), preferably 80 to 120° F. (27 to 49° C.).

All of the above references are incorporated herein by reference in their entirety.

SUMMARY

In one aspect, the invention resides in a process for producing olefins comprising:

(a) providing a vapor product stream from an oxygenate to olefin reaction, said vapor product stream comprising $C_2$ to $C_4$ olefins, $C_2$ to $C_6$ carbonyl compounds and water;

(b) cooling said vapor product stream to provide a first vapor effluent stream comprising no more than 10 wt. % water, and a liquid water-rich stream;

(c) compressing the first vapor effluent stream and a first wash flash vapor stream from a first suction pressure to a second pressure greater than said first suction pressure to form a second vapor effluent stream;

(d) cooling the second vapor effluent stream to form a cooled second effluent stream that is at least partially in the vapor state;

(e) washing at least part of the cooled second effluent stream with a liquid alcohol-containing stream, at a third pressure greater than the first suction pressure but not greater than the second pressure, to produce a wash liquid stream comprising $C_3$ and $C_4$ olefins, and a wash vapor stream, said wash vapor stream having a lower content of $C_2$ to $C_6$ carbonyl compounds than the first vapor effluent stream; and (f) exposing the wash liquid stream to a pressure of at least the first suction pressure but less than the third pressure to form a first wash flash liquid stream and said first wash flash vapor stream, said first wash flash vapor stream being provided for compression (c).

Conveniently, the first vapor effluent stream comprises from about 0.5 to about 5 wt %, such as from about 1 to about 4 wt %, of said carbonyl compounds. In other alternatives, there is more than 5 wt. %, such as no more than 2 wt. % water in the first vapor effluent stream, while in others there is at least 0.1 wt. % and no greater than 5 wt % water.

Conveniently, said first vapor effluent stream produced in (b) is at an initial pressure of from about 1 psig to about 100 psig (108 to 790 kPa), such as from about 5 psig to about 80 psig (135 to 653 kPa), for example from about 10 psig to about 30 psig (170 to 308 kPa). Advantageously, said first suction pressure is no more than 40 psi (275 kPa) below said initial pressure, for example no more than 30 psi (206 kPa), such as no more than 20 psi (138 kPa) or no more than 10 psi (69 kPa) below said initial pressure.

Conveniently, the temperature of the first effluent stream is at least 70° F. (21° C.), such as at least 80° F. (27° C.) and is generally no more than 120° F. (49° C.), such as no more than 110° F. (43° C.), for example no more than 100° F. (38° C.).

Conveniently, said second pressure is no greater than 350 psig (2514 kPa), such as no greater than 200 psig (1480 kPa), for example no greater than 170 psig (1273 kPa) and at least 50 psig (445 kPa), such as at least 100 psig (790 kPa), for example at least 140 psig (1066 kPa).

Conveniently, said cooling (d) produces said second effluent stream with a temperature of at least 70° F. (21° C.), for example at least 80° F. (27° C.), such as at least 90° F. (32° C.), and generally no more than 120° F. (49° C.), such as no more than 110° F. (43° C.), for example no more than 100° F. (38° C.).

Conveniently, said alcohol-containing liquid stream used in the washing (e) comprises methanol and/or ethanol, and preferably methanol. Generally, the alcohol-containing liquid stream used in the washing (e) comprises at least 40 wt % methanol and no greater than 60 wt % water, more particularly at least 75 wt % methanol and no greater than 25 wt % water, such as at least 80 wt % methanol and no greater than 20 wt % water, for example at least 98 wt % methanol and no greater than 2 wt % water, such as at least 99 wt % methanol and no greater than 1 wt % water.

In one embodiment, the washing (e) is conducted by contacting the cooled second effluent with at least 0.03 lb, such as at least 0.05 lb, for example at least 0.07 lb methanol (as pure methanol) per lb of the second effluent stream, and in other embodiments, the washing is conducted by contacting the cooled second vapor effluent stream with the aforementioned minimum methanol proportions per lb of cooled second vapor effluent stream. In a further embodiment, the washing (e) is conducted by contacting the cooled second effluent stream with no greater than 0.5 lb, such as no greater than 0.2 lb, for example no greater than 0.1 lb methanol (as pure methanol) per lb of cooled second effluent stream, and in other embodiments, the washing is conducted by contacting the cooled second vapor effluent stream with the aforementioned maximum methanol proportions per lb of cooled second vapor effluent stream.

Conveniently, the temperature in said washing (e) is at least 70° F. (21° C.), more particularly at least 80° F. (27° C.), such as at least 90° F., and generally no more than 120° F. (49° C.), such as no more than 110° F. (43° C.), for example no more than 100° F. (38° C.).

Conveniently, said third pressure is no greater than 350 psig (2514 kPa), such as no greater than 200 psig (1480 kPa), for example no greater than 170 psig (1273 kPa), and at least 100 psig (790 kPa), such as at least 140 psig (1066 kPa).

Conveniently, the pressure employed in the exposing (f) is from about 1 psig to about 340 psig (108 to 2444 kPa), more particularly from about 5 psig to about 200 psig (135 to 1480 kPa), including from about 5 psig to about 100 psig (135 to 790 kPa), such as from about 5 psig to about 80 psig (135 to 653 kPa), for example from about 10 psig to about 30 psig (170 to 308 kPa).

Conveniently, the temperature employed in the exposing (f) is at least 40° F. (4° C.), such as at least 60° F. (16° C.), and is generally no more than 120° F. (49° C.), more particularly no more than 110° F. (43° C.), for example no more than 100° F. (38° C.), such as no more than 80° F. (27° C.).

Conveniently, said wash liquid stream comprises at least 1 wt. % $C_3$ and $C_4$ olefins, more particularly at least 5 wt. % $C_3$ and $C_4$ olefins, such as at least 10 wt. % $C_3$ and $C_4$ olefins, for example at least 20 wt. % $C_3$ and $C_4$ olefins. In another embodiment, the wash liquid stream comprises no greater than 60 wt. % $C_3$ and $C_4$ olefins, more particularly no greater than 50 wt. % $C_3$ and $C_4$ olefins, such as no greater than 40 wt. % $C_3$ and $C_4$ olefins, for example no greater than 30 wt. % $C_3$ and $C_4$ olefins. An alternative holds there is at least 1 wt. % and no greater than 50 wt. % $C_3$ and $C_4$ olefins in the wash liquid stream. The term "$C_3$ and $C_4$ olefins" means herein the sum total of $C_3$ and $C_4$ olefins.

Another option has the vapor product stream further comprising $C_5$ olefins and the wash liquid stream further comprising $C_5$ olefins. More particularly, the wash liquid comprises at least 1 wt. % $C_3$ to $C_5$ olefins, more particularly at least 5 wt. % $C_3$ to $C_5$ olefins, such as at least 10 wt. % $C_3$ to $C_5$ olefins, for example at least 20 wt. % $C_3$ to $C_5$ olefins. In another embodiment, the wash liquid stream comprises no greater than 75 wt. % $C_3$ to $C_5$ olefins, more particularly no greater than 60 wt. % $C_3$ to $C_5$ olefins, such as no greater than 50 wt. % $C_3$ to $C_5$ olefins, for example no greater than 40 wt. % $C_3$ to $C_5$ olefins. An alternative holds there is at least 1 wt. % and no greater than 60 wt. % $C_3$ to $C_5$ olefins in the wash liquid stream. The term "$C_3$ to $C_5$ olefins" means herein the sum total of $C_3$, $C_4$ and $C_5$ olefins.

Another embodiment holds that the cooling (b) is conducted in a device such as an indirect heat exchanger, or in a direct contact quenching device, more particularly a quench tower. A further manifestation includes using both an indirect heat exchanger and a direct contact quenching device in combination to conduct the cooling (b).

In one embodiment, the cooling (d) produces a cooled second vapor effluent stream and a second liquid effluent stream, said cooled second vapor effluent stream vapor being washed (e), and said second liquid effluent stream being exposed to a pressure of at least the first suction pressure and no greater than the third pressure to form a second wash flash liquid stream and a second wash flash vapor stream, said second wash flash vapor stream also being provided for compression (c). Conveniently, the temperature employed in the exposing of the second liquid effluent stream is at least 40° F. (4° C.), such as at least 60° F. (16° C.), and is generally no more than 120° F. (49° C.), more particularly no more than 110° F. (43° C.), for example no more than 100° F. (38° C.), such as no more than 80° F. (27° C.).

In another embodiment, the exposing (f) occurs in a vessel, and the second liquid effluent stream is also introduced to said vessel, optionally after being combined with the wash liquid stream, to provide the first and second wash flash vapor streams as a common stream for compression (c), and the first and second wash flash liquid streams as a common stream. Conveniently, the first effluent stream is also introduced to the vessel used in (f) whereby the first effluent stream, and the first and second wash flash vapor streams are provided as a common stream for compression in step (c).

In an alternative embodiment, the cooling (b) and exposing (f) are effected in the same device to provide the first vapor effluent stream and first wash flash vapor stream as a common stream for compression (c), and the liquid water-rich stream and first wash flash liquid stream as a common stream. Conveniently, the second liquid effluent stream is also provided to the same cooling device, optionally after being combined with the wash liquid stream, to provide the first vapor effluent stream, the first wash flash vapor stream and the second wash flash vapor stream as a combined stream for compression (c) and the liquid water-rich stream, first wash flash liquid stream and second wash flash liquid stream as a common stream.

In still a further aspect, the invention resides in a process for producing olefins comprising:
(a) providing a vapor product stream from an oxygenate to olefin reaction, said product comprising $C_2$ to $C_4$ olefins, $C_2$ to $C_6$ carbonyl compounds and water;
(b) cooling said vapor product stream to provide a first vapor effluent stream at a first pressure no greater than the reaction pressure and comprising no more than 10 wt. % water, and a liquid water-rich stream;
(c) compressing the first vapor effluent stream from a first suction pressure that is no greater than said first pressure to an intermediate pressure greater than said first pressure to form an intermediate effluent stream;
(d) cooling the intermediate effluent stream to form an intermediate effluent vapor stream and an intermediate effluent liquid stream;
(e) compressing the intermediate effluent vapor stream from an intermediate suction pressure that is no greater than said intermediate pressure to a second pressure greater than said intermediate pressure to form a second effluent stream;
(f) cooling the second effluent stream to form a cooled second effluent stream that is at least partially vapor;
(g) washing at least part of the cooled second effluent stream with a liquid alcohol-containing stream in a vapor-liquid contacting device, at a third pressure greater than the intermediate suction pressure but not greater than the second pressure, to produce a wash liquid stream comprising $C_3$ and $C_4$ olefins, and a wash vapor stream, said wash vapor stream having a lower content of $C_2$ to $C_6$ carbonyl compounds than the first vapor effluent stream; and
(h) exposing at least part of the wash liquid stream to a pressure of at least the first suction pressure and less than the third pressure to form a first wash flash liquid stream and a first wash flash vapor stream, said first wash flash vapor stream being provided for compression (c) along with the first vapor effluent stream, or for compression (e) along with the intermediate effluent vapor stream, or both.

Conveniently, said intermediate effluent stream is cooled (d) to a temperature of at least 70° F. (21° C.), for example at least 80° F. (27° C.), such as at least 90° F. (32° C.), and generally no more than 120° F. (49° C.), such as no more than 110° F. (43° C.), for example no more than 100° F. (38° C.), to form said intermediate effluent vapor stream and said intermediate effluent liquid stream.

In one embodiment, the wash liquid stream in (h) is exposed to a pressure of at least the intermediate suction pressure and said first wash flash vapor stream is provided for compression (e) along with the intermediate effluent vapor stream.

In another embodiment, the cooling (f) produces a cooled second vapor effluent stream and a second liquid effluent stream, said cooled second vapor effluent stream being provided to the washing (g), and said second liquid effluent stream being exposed to a pressure of at least the first suction pressure and no greater than the third pressure to form a second wash flash liquid stream and a second wash flash vapor stream, said second wash flash vapor stream also being provided for compression (c) along with the first effluent stream, or for compression (e) along with the intermediate effluent vapor stream, or both. Conveniently, said second liquid effluent stream is exposed to a pressure of at least the intermediate suction pressure and said second wash flash vapor stream is provided for compression (e) along with the intermediate effluent vapor stream. Conveniently, the exposing (h) occurs in a vessel, and the second liquid effluent stream is also introduced to said vessel, optionally after being combined with said wash liquid stream, to provide the first wash flash vapor stream and second wash flash vapor stream as a common stream for compression (c) and/or compression (e), and to provide the first wash flash liquid and the second wash flash liquid as a common stream. In addition, the cooled intermediate effluent stream from (d) may be introduced into the vessel, optionally after being combined with the second liquid effluent stream and/or the wash liquid stream, to provide the first wash flash vapor stream and the second wash flash vapor stream and the intermediate effluent vapor stream as a common stream for compression (e), and the first wash flash liquid and the second wash flash liquid and the intermediate effluent liquid stream as a common stream.

Alternatively, the cooled second effluent stream may be introduced into a vessel to form the cooled second vapor effluent stream and the second liquid effluent stream, independent of the wash liquid stream or the cooled intermediate effluent stream. Likewise, the cooled intermediate effluent stream may be introduced into a vessel to form the intermediate effluent vapor stream and the intermediate effluent liquid stream, independent of the wash liquid stream or the second liquid effluent stream. Conveniently, the temperature employed in the exposing of the cooled second effluent stream or the cooled intermediate effluent stream, for example in a vessel, is at least 40° F. (4° C.), such as at least 60° F. (16° C.), and is generally no more than 120° F. (49° C.), more particularly no more than 110° F. (43° C.), for example no more than 100° F. (38° C.), such as no more than 80° F. (27° C.).

In another embodiment, the intermediate effluent liquid stream is exposed to a pressure of at least the first suction pressure and less than the intermediate pressure to form an intermediate flash vapor effluent stream and an intermediate flash liquid effluent stream. The intermediate flash vapor effluent stream is provided for compression (c) along with the first vapor effluent stream. Alternatively, the intermediate flash vapor effluent stream is provided, possibly along with another intermediate effluent stream or intermediate effluent vapor stream, for compression in one stage of a plurality of stages of compression, to a pressure no greater than the intermediate pressure. Conveniently, the pressure employed in the exposure of the intermediate effluent liquid to form the intermediate flash vapor effluent and intermediate flash liquid effluent streams, for example in a vessel, is from about 1 psig to about 340 psig (108 to 2444 kPa), more particularly from about 5 psig to about 200 psig (135 to 1480 kPa), including from about 5 psig to about 100 psig (135 to 790 kPa), such as from about 5 psig to about 80 psig (135 to 653 kPa), for example from about 10 psig to about 30 psig (170 to 308 kPa). Conveniently, the temperature employed in the exposure of the intermediate effluent liquid to form the intermediate flash vapor effluent and intermediate flash liquid effluent streams is, for example in a vessel, at least 40° F. (4° C.), such as at least 60° F. (16° C.), and is generally no more than 120° F. (49° C.), more particularly no more than 110° F. (43° C.), for example no more than 100° F. (38° C.), such as no more than 80° F. (27° C.).

In still yet a further aspect, the invention resides in a process for producing olefins comprising:

(a) providing a vaporous reaction product from an oxygenate to olefin reaction, said product comprising $C_2$ to $C_4$ olefins, oxygenated hydrocarbons and water;

(b) condensing the vaporous reaction product in a quenching device to provide a vaporous first effluent stream at a first pressure and comprising no more than 10 wt. % of the water in the reaction product, and a liquid water-rich stream;

(c) introducing the vaporous first effluent stream and an intermediate effluent liquid stream into a first vessel, optionally after combining said first effluent stream and the intermediate effluent liquid stream, to form a flash vapor added first effluent stream and a second vessel liquid stream;

(d) compressing the flash vapor added first effluent stream to an intermediate pressure to form an intermediate effluent stream;

(e) cooling the intermediate effluent stream and introducing said cooled intermediate effluent stream into a second vessel together with a second liquid effluent stream and a wash liquid stream to form an intermediate effluent vapor stream and said intermediate effluent liquid stream;

(f) compressing the intermediate effluent vapor stream to a second pressure greater than said intermediate pressure to form a second effluent stream;

(g) cooling the second effluent stream and introducing said cooled second effluent stream into a third vessel to form a cooled second vapor effluent stream and said second liquid effluent stream; and (h) washing the cooled second vapor effluent stream with an alcohol-containing liquid stream in a vapor-liquid contacting device, at a third pressure of greater than the intermediate pressure but no greater than the second pressure, to produce said wash liquid stream and a wash vapor stream, said wash vapor stream having a lower content of oxygenated hydrocarbons than the first effluent stream.

Conveniently, the intermediate pressure is less than 350 psig (2514 kPa), such as less than 200 psig (1480 kPa), for example less than 170 psig (1273 kPa), and is greater than 5 psig (136 kPa), for example greater than 20 psig (239 kPa), such as greater than 40 psig (377 kPa).

Advantageously, said intermediate suction pressure at the entrance to the compression device is no more than 40 psi (275 kPa) below said intermediate pressure, for example no more than 30 psi (206 kPa), such as no more than 20 psi (138 kPa) or no more than 10 psi (69 kPa) below said intermediate pressure.

As used herein, the term "$C_x$ hydrocarbon" indicates aliphatic, olefin, diolefin, acetylene, or cyclic variations thereof, or in appropriate cases aromatic, hydrocarbon molecules having the number of carbon atoms represented by the subscript "x" Similarly, the term "$C_x$-containing stream" means the stream contains $C_x$ hydrocarbon. The more specific molecule is represented by a more explicit term in place of "hydrocarbon", so that, for example, "$C_4$ olefin" indicates butene-1, or butene-2, or isobutene, or combinations thereof. The term "$C_x$+ hydrocarbons" indicates those molecules noted above having the number of carbon atoms represented by the subscript "x" or greater. For example, "$C_4$+ hydrocarbons" would include $C_4$, $C_5$ and higher carbon number hydrocarbons. Similarly "$C_x$– hydrocarbons" indicates those molecules noted above having the number of carbon atoms represented by the subscript "x" or fewer. As used herein, hydrocarbons do not contain an oxygen molecule and thus are not to be confused with the term oxygenate or its various more specific forms, such as alcohol, ether, aldehyde, ketone or carbonyl.

As used herein, the term $C_2$ to $C_6$ carbonyl compounds is defined as meaning one or more molecules containing from 2 to 6 carbon atoms that further comprise at least one oxygen atom in an aldehyde (oxygen that has a double bond to a carbon atom that in turn has a single bond to one other carbon atom and one hydrogen atom) or ketone (oxygen that has double bond to a carbon atom that in turn has a single bond to each of two other carbon atoms) moiety.

DETAILED DESCRIPTION OF THE EMBODIMENTS

Figure 1:
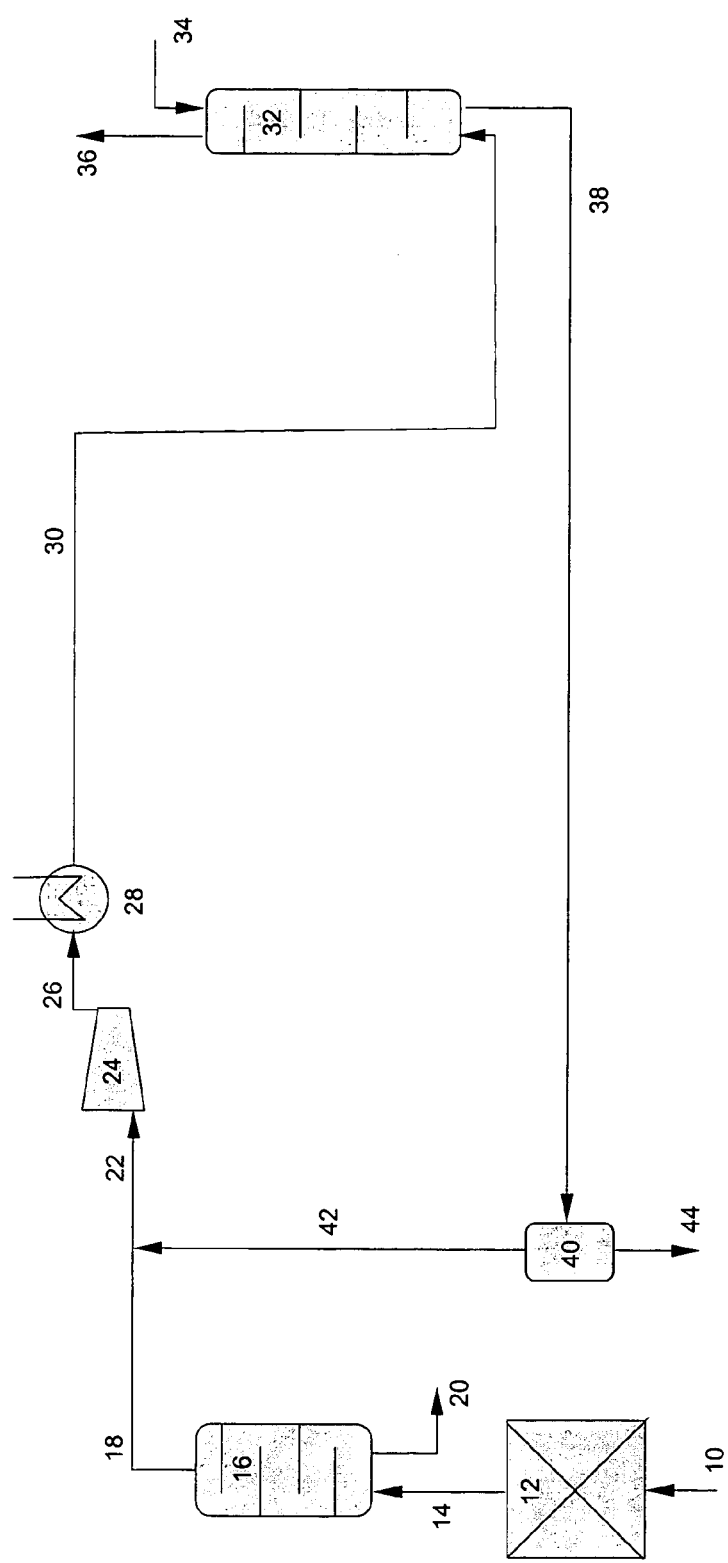
FIG. 1 is a schematic flow diagram illustrating a process according to one example of the invention.

Molecular Sieves and Catalysts Thereof for Use in OTO Conversion

Molecular sieves suited to use for converting oxygenates to olefins (OTO) have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials.

Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference.

Non-limiting examples of these molecular sieves are the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves of a framework-type selected from the group consisting of AFO, AEL, EUO, HEU, FER, MEL, MFI, MTW, MTT, TON, and substituted forms thereof; and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON. In one embodiment, the molecular sieve used in the process of the invention has an AEI topology or a CHA topology, or a combination thereof, preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Volume 137, pages 1-67, Elsevier Science, B. V., Amsterdam, Netherlands (2001).

The small, medium and large pore molecular sieves have from a 4-ring to a 12-ring or greater framework-type. In one embodiment, the molecular sieves used herein have 8-, 10- or 12-ring structures or larger and an average pore size in the range of from about 3 Å to 15 Å. More typically, the molecular sieves utilized in the invention, such as silicoaluminophosphate molecular sieves, have 8-rings and an average pore size less than about 5 Å, such as in the range of from 3 Å to about 5 Å, for example from 3 Å to about 4.5 Å, particularly from 3.5 Å to about 4.2 Å.

Molecular sieves used herein typically have two or more [$SiO_4$], [$AlO_4$] and/or [$PO_4$] tetrahedral units. These silicon, aluminum and/or phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [$QO_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), International Patent Publication No. WO 01/64340 published Sep. 7, 2001 (thorium containing molecular sieve), and R. Szostak, *Handbook of Molecular Sieves,* Van Nostrand Reinhold, New York, N.Y. (1992), which are all herein fully incorporated by reference.

The more preferred silicon, aluminum and/or phosphorous containing molecular sieves include aluminophosphate (ALPO) molecular sieves, silicoaluminophosphate (SAPO) molecular sieves and substituted, preferably metal substituted, forms thereof. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [$MeO_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

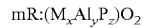

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanides of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. Patent Application Publication No. 2002/0165089 published Nov. 7, 2002 and International Patent Publication No. WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

The molecular sieves useful for oxygenates to olefins conversion processes are synthesized and then made or formulated into catalysts by combining the synthesized molecular sieves with a binder and/or a matrix material to form a molecular sieve catalyst composition. This molecular sieve catalyst composition is formed into useful shaped and sized particles by well-known techniques such as spray drying, pelletizing, extrusion, and the like.

Oxygenate to Olefins (OTO) Process

The feedstock to an oxygenate to olefins process comprises one or more oxygenates, more specifically, one or more organic compound(s) containing at least one oxygen atom. Typically, the oxygenate in the feedstock comprises one or more alcohol(s), generally aliphatic alcohol(s) where the aliphatic moiety of the alcohol(s) has from 1 to 20 carbon atoms, such as from 1 to 10 carbon atoms, and conveniently from 1 to 4 carbon atoms. The alcohols useful as feedstock in an oxygenate to olefins process include lower straight and branched chain aliphatic alcohols and their unsaturated counterparts.

Non-limiting examples of suitable oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. Typically, the feedstock is selected from one or more of methanol, ethanol, dimethyl ether and diethyl ether, especially methanol and dimethyl ether, and preferably methanol.

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition. Diluent(s) may comprise from about 1 mole % to about 99 mole % of the total feedstock.

In the OTO process, the various feedstocks discussed above, particularly a feedstock containing an alcohol, are converted over a molecular sieve catalyst, primarily into one or more olefin(s). The olefin(s) or olefin monomer(s) produced from the feedstock typically have from 2 to 30 carbon atoms, such as 2 to 8 carbon atoms, for example 2 to 6 carbon atoms, especially 2 to 4 carbons atoms, and preferably are ethylene and/or propylene.

The present process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system would conveniently include a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of liquid feedstock fed separately or jointly with a vapor feedstock, to the reactor system is in the range of from 0.1 weight percent to about 85 weight percent, such as from about 1 weight percent to about 75 weight percent, for example from about 5 weight percent to about 65 weight percent based on the total weight of the feedstock including any diluent contained therein. The liquid and vapor feedstocks are preferably of similar or the same composition, or contain varying proportions of the same or different feedstock with the same or different diluent.

The feedstock entering the reactor system is preferably converted, partially or fully, in the first reactor zone into a vapor product stream that enters the disengaging vessel along with the coked catalyst composition. In the preferred embodiment, cyclone(s) are provided within the disengaging vessel to separate the coked catalyst composition from the vapor product stream containing one or more olefin(s) within the disengaging vessel. Although cyclones are preferred, gravity effects within the disengaging vessel can also be used to separate the catalyst composition from the vapor product stream. Other methods for separating the catalyst composition from the vapor product stream include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are disclosed in U.S. Pat. No. 6,290,916 (controlling moisture), which is herein fully incorporated by reference.

The regenerated catalyst composition withdrawn from the regeneration system, preferably from a catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Flu-*

*idized Beds*, Grace, Avidan and Knowlton, eds., Blackie, 1997 (336-337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The vapor product stream is withdrawn from the disengaging system and passed to a recovery system for separating and purifying the olefins and other useful components in the product stream.

OTO Product Recovery Process

The vapor product stream from the oxygenate to olefin conversion process described above is a complex mixture comprising the desired $C_2$ to $C_5$ olefins, unconverted oxygenates, by-product oxygenates (including $C_2$ to $C_6$ aldehydes and ketones), heavier hydrocarbons (including aromatics) and large amounts of water.

On leaving the OTO reactor system, the vapor product stream is at reaction temperature and pressure and hence is initially cooled in a quench device. The quench device removes heat from the vapor product stream, and may comprise a traditional indirect heat exchanger, for example using cooling water or air on the shell or open side with the vapor product stream within tubes, or a direct contact device such as a traditional quench tower employing water as the quench medium. As a result of this cooling, water from the vapor product stream will condense to the liquid phase while the bulk of the hydrocarbons remain in the vapor phase. The liquid water phase is then separated from the vapor phase by conventional means. In an indirect heat exchanger, for example, the water may be collected and removed from a boot provided at the bottom of the exchanger shell, or the entire condensed vapor product stream may be passed to a vessel, such as a drum, to provide such liquid-vapor separation. In the quench tower, the water may be collected in and exit from the bottom of the tower shell. In any case, most of the water (generally at least 90 wt %) in the vapor product stream is condensed and is removed from the bottom of the quench device as a liquid water-rich bottoms stream. The light hydrocarbons and light oxygenates in the product stream are removed from the top of the heat exchanger or quench tower as a first vapor effluent stream at a first pressure.

The water-rich bottoms stream from the quench device will contain various other materials in addition to water, such as unreacted oxygenate feedstock, e.g., methanol, and other oxygenates created as byproducts of the oxygenate to olefins reaction, for example, but not limited to, ethanol, ethanal, propanal, acetone, butanone, dimethyl ether, methyl ethyl ether, acetic acid and propionic acid. The proportions of these oxygenates in the water-rich bottoms stream may vary widely dependent upon the nature of the oxygenate to olefin reactor, including feedstock, catalyst, WHSV, temperature and pressure. Further, the proportions of these oxygenates in the water-rich bottoms stream may vary widely dependent upon the specifics of the quench tower, such as the pressure, temperature and height of the tower and nature of the exchanger or tower internals.

Regardless of the exact composition, the liquid water-rich bottoms stream will need to undergo further processing to provide components in an appropriate state for use or further treatment, e.g., provide a water stream low enough in organic content for typical water waste treatment, or provide an oxygenate stream low enough in water content for use as fuel or for addition to some point in the oxygenate to olefins process or apparatus. Examples of such treatment can be found in U.S. Pat. Nos. 6,121,504, 6,403,854 and 6,459,009 and U.S. patent application Ser. No. 10/720,505 filed Nov. 24, 2003.

In one embodiment, the liquid water-rich bottoms stream is directed to a water-oxygenate fractionation tower, e.g., a water-methanol fractionation tower, which is operated to separate methanol and other oxygenates as an overhead, e.g., greater than about 20 wt % oxygenates (with the balance being largely water), and substantially pure water as a bottoms stream, typically, greater than about 90 wt % water, say, greater than about 95 wt % water, e.g., greater than about 99 wt % water. The oxygenate-rich overhead product of the fractionation tower can be used for various purposes, including as a feedstock to the OTO reactor along with the primary oxygenate feedstock. If the oxygenate-rich overhead product is taken as a vapor, this provides vaporized methanol/oxygenate feed to the reactor with virtually no incremental heat input beyond that already required in the reboiler of the methanol-water fractionation tower, with no incremental heat load in the primary feed vaporization section of the OTO reactor.

The first vapor effluent stream exiting as overhead from the quench tower is typically at an initial pressure of from about 1 psig to about 100 psig (108 to 790 kPa), such as from about 5 psig to about 80 psig (135 to 653 kPa), for example from about 10 psig to about 30 psig (170 to 308 kPa). Conveniently, the temperature of the first vapor effluent stream is at least 80° F. (27° C.) and generally no more than 120° F. (49° C.), such as no more than 110° F. (43° C.), for example no more than 100° F. (38° C.). The first vapor effluent stream normally comprises from about 0.5 to about 5 wt %, such as from about 1 to about 4 wt %, of $C_2$ to $C_6$ carbonyl compounds and no more than 10 wt %, for example no more than 5 wt %, such as no more than 2 wt %, water.

After exiting the quench device, the first vapor effluent stream is in communication with a vapor compression device, conveniently such as a traditional mechanical reciprocating, centrifugal or axial compressor. Even non-mechanical devices like an ejector, such as a steam ejector, may be used, but are not preferred. The communication typically includes passage through a pipe, potentially further comprising other process elements such as vessels, instrumentation (e.g. a flow metering orifice plate) or valves, such as control valves. Such communication will cause a reduction in the pressure of the first vapor effluent prior to reaching the suction of the compression device at a first suction pressure. Generally the communication path is designed to preserve as much pressure of the first vapor effluent stream as practical, thus saving compression costs. Advantageously, the first suction pressure at the entrance to the compression device is no more than 40 psi (275 kPa) below the initial pressure, for example no more than 30 psi (206 kPa), such as no more than 20 psi (138 kPa) or no more than 10 psi (69 kPa) below the initial pressure.

Following communication from the quench device, to the suction of the compression device, the first vapor effluent stream is compressed to form a second vapor effluent stream at a second pressure that is greater than the first pressure. The second vapor effluent stream is then cooled, for example in an indirect heat exchanger, to produce a cooled second effluent stream that is at least partially in the vapor state.

Conveniently, the second pressure is less than 350 psig (2514 kPa), such as less than 200 psig (1480 kPa), for example less than 170 psig (1273 kPa), and greater than 100 psig (790 kPa), such as greater than 140 psig (1066 kPa). Conveniently, the cooled second effluent is at a temperature of at least 70° F. (21° C.), for example at least 80° F. (27° C.), such as at least 90° F., and generally no more than 120° F. (49° C.), such as no more than 110° F. (43° C.), for example no more than 100° F. (38° C.).

The cooled second effluent stream is then subjected to a first washing step with a liquid alcohol-containing stream in a first vapor-liquid contacting device at a third pressure not greater than the second pressure. Conveniently, the third pressure is less than 350 psig (2514 kPa), such as less than 200 psig (1480 kPa), for example less than 170 psig (1273 kPa), and greater than 100 psig (790 kPa), such as greater than 140 psig (1066 kPa). The first washing step serves to remove aldehydes and ketones from the cooled second effluent stream and produces a wash vapor stream, containing the desired olefin product, and a wash liquid stream. Conveniently, said wash vapor stream comprises less than 0.5 wt. %, such as less than 0.1 wt %, for example less than 500 ppmwt, of $C_2$ to $C_6$ carbonyl compounds.

Conveniently, said liquid alcohol-containing stream used in the first washing step comprises methanol and/or ethanol, and preferably methanol, and thus is a liquid methanol-containing stream. The methanol employed as a liquid methanol-containing stream can contain water and traces (such as less than 2 wt %, or less than 1 wt %, or less than 0.5 wt % or less than 0.1 wt %) of other alcohols and hydrocarbons. In general, methanol is more effective than water and other alcohols in removing such carbonyl species from hydrocarbons in a vapor-liquid wash. Typically, therefore, the alcohol-containing liquid stream used in the first washing step comprises at least 40 wt % methanol and less than 60 wt % water, such as at least 75 wt % methanol and less than 25 wt % water, for example at least 90 wt % methanol and less than 10 wt % water, or such as at least 99 wt % methanol and less than 1 wt % water.

In general, the temperature employed in the first washing step should be no more than 120° F. (49° C.) so as to enhance the oxygenate adsorption capacity of the alcohol, especially methanol, and limit the amount of vaporized alcohol exiting the first vapor-liquid contacting device with the wash vapor stream. In addition, the temperature employed in the first washing step is generally at least 70° F. (21° C.) so as to limit the amount of hydrocarbons adsorbed by the alcohol to acceptable levels. Conveniently, the temperature of the first washing step is at least 80° F. (27° C.), such as at least 90° F., and no more than 110° F. (43° C.), for example no more than 100° F. (38° C.).

Conveniently, where the alcohol utilized is methanol, the amount of methanol employed in the first washing step is at least 0.03 lb (as pure methanol) per lb of the cooled second effluent stream so as to ensure that there is sufficient methanol to (1) achieve the required low level of oxygenate in the $C_4$ component of wash vapor stream and (2) prevent the formation of a third, aqueous liquid phase in the first vapor-liquid contacting device. In addition, the amount of methanol employed in the first washing step is generally no more than 0.5 lb (as pure methanol) per lb of the cooled second effluent stream so as to limit the amount of prime olefin (ethylene and propylene) removed into the wash liquid stream. Preferably, the amount of methanol employed is as at least 0.05 lb, such as at least 0.06 lb, for example at least 0.07 lb methanol (as pure methanol) per lb of the cooled second effluent stream. In addition, the amount of methanol employed is preferably no more than 0.2 lb, such as no more than 0.15 lb, for example no more than 0.1 lb methanol (as pure methanol) per lb of the cooled second effluent stream.

In one embodiment, the first vapor-liquid contacting device is a countercurrent fractional distillation tower, in which the cooled second effluent stream is directed into the bottom of the tower and methanol is directed into the top of the tower. The wash vapor stream exits the tower as overhead while the wash liquid stream exits as a bottoms stream.

In the course of washing the cooled second effluent stream with an alcohol, desirable hydrocarbons such as $C_3$, $C_4$ and $C_5$ olefins will be absorbed by the alcohol (in addition to absorbing the undesirable by-product oxygenates, including $C_2$ to $C_6$ aldehydes and ketones), and will exit with the wash liquid. Under certain alcohol wash conditions, such as higher wash rates and pressure and lower temperatures, small but appreciable amounts of ethylene will be absorbed. In an embodiment, the wash liquid stream will contain at least 1 wt. % $C_3$ and $C_4$ olefins, more particularly at least 5 wt. % $C_3$ and $C_4$ olefins, such as at least 10 wt. % $C_3$ and $C_4$ olefins, for example at least 20 wt. % $C_3$ and $C_4$ olefins. In another embodiments, the wash liquid stream comprises no greater than 60 wt. % $C_3$ and $C_4$ olefins, more particularly no greater than 50 wt. % $C_3$ and $C_4$ olefins, such as no greater than 40 wt. % $C_3$ and $C_4$ olefins, for example no greater than 30 wt. % $C_3$ and $C_4$ olefins. An alternative holds there is at least 1 wt. % and no greater than 50 wt. % $C_3$ and $C_4$ olefins in the wash liquid stream.

Another option has the wash liquid stream further comprising $C_5$ olefins. More particularly, the wash liquid comprises at least 1 wt. % $C_3$ to $C_5$ olefins, more particularly at least 5 wt. % $C_3$ to $C_5$ olefins, such as at least 10 wt. % $C_3$ to $C_5$ olefins, for example at least 20 wt. % $C_3$ to $C_5$ olefins. In another embodiment, the wash liquid stream comprises no greater than 75 wt. % $C_3$ to $C_5$ olefins, more particularly no greater than 60 wt. % $C_3$ to $C_5$ olefins, such as no greater than 50 wt. % $C_3$ to $C_5$ olefins, for example no greater than 40 wt. % $C_3$ to $C_5$ olefins. An alternative holds there is at least 1 wt. % and no greater than 60 wt. % $C_3$ to $C_5$ olefins in the wash liquid stream.

The process of the present invention seeks to recover these $C_2$ to $C_5$ olefins into the wash vapor while still providing the desired removal of $C_2$ to $C_6$ aldehydes and ketones from the wash vapor. This is effected by exposing the wash liquid to a pressure lower than third pressure, to promote a vapor-liquid flash of the wash liquid and form a first wash flash vapor stream and a first wash flash liquid stream. The desirable hydrocarbons tend to concentrate in the first wash flash vapor stream, while the undesirable by-product oxygenates tend to concentrate in the first wash flash liquid stream. The first wash flash vapor stream is then recycled to the suction of the compression device along with the first vapor effluent stream, and the wash flash liquid stream is removed for further processing or discarded. Thus, it is useful to utilize a pressure to which the wash liquid is exposed that is higher than the first suction pressure.

Generally, the pressure to which the wash liquid is exposed to generate the first wash flash liquid and the first wash flash vapor is from about 1 psig to about 340 psig (108 to 2444 kPa), more particularly from about 5 psig to about 200 psig (135 to 1480 kPa), including from about 5 psig to about 100 psig (135 to 790 kPa), such as from about 5 psig to about 80 psig (135 to 653 kPa), for example from about 10 psig to about 30 psig (170 to 308 kPa). Further, the temperature to which the wash liquid is exposed is at least 40° F. (4° C.), such as at least 60° F. (16° C.), and is generally no more than 120° F. (49° C.), more particularly no more than 110° F. (43° C.), for example no more than 100° F. (38° C.), such as no more than 80° F. (27° C.).

As noted earlier the cooled second effluent stream will be at least partially in the vapor state, and thus may be partially in the liquid state, dependent upon the conditions employed in the cooling. It may be beneficial to segregate this stream into a separate cooled second vapor effluent stream and a second liquid effluent stream, and provide the cooled second vapor effluent stream for alcohol washing at the same conditions that have been discussed for the cooled second effluent stream, independent of the second liquid effluent stream. Further, one may then choose to expose the second liquid effluent stream to conditions effective to promote a vapor-liquid flash of the stream, according to the same conditions that have been discussed for the wash liquid, to provide a second wash flash vapor stream and a second wash flash liquid stream. The second wash flash vapor may then be introduced to the suction of the compression device providing the second pressure, along with the first wash flash vapor.

A vapor-liquid flash of a stream, such as the wash liquid or second liquid effluent, may be effected in a number of different ways. For example, the wash liquid may be provided to a simple vessel of the appropriate volume and configuration, such as a traditional flash drum, that readily provides for separation of the liquid and vapor streams, and exit of the streams from at or near the bottom and top of the vessel, respectively. Alternatively, a vapor-liquid flash may be effected in other items of process equipment, such as heat exchangers and quench towers, or other equipment that provides both suitable flash volume and heat transfer capabilities simultaneously. A separate vessel or item of equipment may be used for each stream, independently providing vapor and liquid streams at the same or different conditions, or more than one stream may be provided to the same vessel or item of equipment to provide a common vapor and a common liquid stream.

With regard to common equipment items being used to expose various streams to process conditions that promote a vapor-liquid flash, a notable example is putting the wash liquid and the second liquid effluent stream in the same vessel, such as a flash drum, with both streams then exposed at the same conditions within the vessel to provide the first and second wash flash vapor streams as a common stream for compression to the second pressure, and provide the first and second wash flash liquid streams as a common stream for a suitable disposition. Similarly, the wash liquid, second liquid effluent and first vapor effluent stream may be provided to the same vessel at the same conditions to provide the first and second wash flash vapor streams and the first vapor effluent stream as a common stream for compression to the second pressure, and provide the first and second wash flash liquid streams as a common stream. The wash liquid stream, second liquid effluent stream or first vapor product stream may, if desired, be mixed in any combination prior to introduction to a common vessel or other equipment item.

In yet another embodiment involving the common disposition of various streams of the present invention, all or part of the wash liquid stream, the second liquid effluent stream, or both may be provided to the same cooling device, e.g. the quench tower, to which the vapor product stream is introduced. This will provide the first and second wash flash vapor streams and the first vapor effluent stream as a common stream for compression to the second pressure, and provide the first and second wash flash liquid streams and the liquid water-rich bottoms stream as a common stream.

In the present invention, it may be desirable to bring the first vapor effluent stream to the second pressure using more than one stage of compression, going through one or more intermediate pressures between the first suction pressure and the second pressure. This may be beneficial, for example, when operating with a relatively low initial pressure or a relatively high second pressure, or particularly with both, where it may be impractical or inefficient to achieve the desired pressure increase using a single stage of compression. It may also be desirable to cool the intermediate effluent stream discharged from one compression stage prior to passing it on to the suction of another compression stage to achieve a further increase in pressure, and so on until the second vapor effluent stream at the desired second pressure is achieved.

In one embodiment, the intermediate effluent from one compression stage is cooled such that it remains substantially in the vapor state (say, least 95 wt. %, or at least 99 wt. %, or all in the vapor state) prior to being passed on in total to the suction of another compression stage to achieve a further increase in pressure, and so on until the second effluent stream at the desired second pressure is obtained. This is beneficial inasmuch as most types of mechanical compression equipment do not function well with liquid feeds.

In another manifestation where compression and cooling of the first vapor effluent stream to produce the second vapor effluent stream occur in a plurality of stages, cooling of an intermediate effluent stream (or streams) is conducted to effect partial condensation, and an intermediate effluent liquid stream (or streams) is removed from the first vapor effluent stream, with the resulting intermediate effluent vapor stream then being passed to the next stage of compression. Conveniently, the intermediate effluent liquid and intermediate effluent vapor stream (or streams) are separated in a vessel such as a knock-out drum provided after a given compression/cooling stage. The resultant intermediate effluent vapor stream is then passed to the next stage of compression, potentially repeating compression/cooling, until the second effluent stream at the desired second pressure is obtained. The second effluent stream need not comprise all of the material provided in the first vapor effluent stream. The intermediate effluent liquid streams can, for example, be recycled back to the OTO reactor, conveniently by way of a water-oxygenate fraction tower, among other dispositions discussed below.

In one specific embodiment involving multiple stages of compression, the first vapor effluent stream is compressed from a first suction pressure to an intermediate pressure to form an intermediate effluent stream. The intermediate effluent stream is cooled in cooling device, for example, an indirect heat exchanger, the product of which is a cooled intermediate effluent stream. The cooling of the intermediate effluent stream causes condensation of a part of the cooled intermediate effluent stream, and an intermediate effluent vapor stream and an intermediate effluent liquid stream are separated therefrom, for example in a vessel. The intermediate effluent vapor stream is then further compressed from an intermediate suction pressure that is no greater than the intermediate pressure to the second pressure, thus forming the second effluent stream. The second effluent stream is cooled to an at least partially vaporized state, and potentially segregated into a second liquid effluent stream and a cooled second vapor effluent stream, and the second effluent stream or cooled second vapor effluent stream is alcohol washed as noted previously to form the wash vapor stream and the wash liquid stream. In this embodiment, all or part of the wash liquid stream is subjected to a vapor-liquid flash as noted previously, and the resultant first wash flash vapor may be provided along with the intermediate effluent vapor stream at the intermediate suction pressure to be compressed and form the second effluent stream at the second pressure, or provided along with the first vapor effluent stream at the first suction pressure to be compressed and form the intermediate effluent stream at the intermediate pressure, or both.

Conveniently, the intermediate pressure is less than 350 psig (2514 kPa), such as less than 200 psig (1480 kPa), for example less than 170 psig (1273 kPa), and is greater than 5 psig (136 kPa), for example greater than 20 psig (239 kPa), such as greater than 40 psig (377 kPa). Advantageously, for considerations and reasons similar to those noted above for the first suction pressure, the intermediate suction pressure is no more than 40 psi (275 kPa) below the intermediate pressure, for example no more than 30 psi (206 kPa), such as no more than 20 psi (138 kPa) or no more than 10 psi (69 kPa) below the intermediate pressure.

In another aspect involving an intermediate effluent stream, the second liquid effluent stream is exposed to a pressure of at least the first suction pressure and no greater than the third pressure to form a second wash flash liquid and a second wash flash vapor, and the second wash flash vapor is provided for compression from the intermediate suction pressure to the second pressure along with the intermediate vapor stream and possibly the first wash flash vapor stream, or for compression from the first suction pressure to the intermediate pressure with the first vapor effluent stream and possibly the first wash flash vapor stream, or both. More particularly, the second liquid effluent stream is exposed to a pressure of at least the intermediate suction pressure and no greater than the third pressure, and the second wash flash vapor is provided for compression from the intermediate suction pressure to the second pressure along with the intermediate effluent vapor stream.

In yet another manifestation of the present invention involving an intermediate effluent stream at an intermediate pressure, the intermediate effluent stream is cooled to produce a cooled intermediate effluent stream that is segregated into an intermediate effluent liquid stream and an intermediate effluent vapor stream. The intermediate effluent liquid stream is exposed to a pressure of at least the first suction pressure and less than the intermediate pressure to form an intermediate flash vapor effluent stream and an intermediate flash liquid effluent stream. The resulting intermediate flash vapor effluent stream is provided for compression, in one stage of a plurality of stages, to a pressure that is no greater than the intermediate pressure from which the intermediate effluent liquid stream was derived, potentially along with another intermediate vapor stream or the first vapor effluent stream. In a specific embodiment of this type, the intermediate flash vapor effluent stream is combined with the first vapor effluent stream to form a flash vapor added first effluent stream that is compressed from the first suction pressure to an intermediate pressure to form an intermediate effluent stream.

As noted earlier, any vapor-liquid flash may take place in a vessel, and one or more of the streams may be directed to a common vessel, independently or following mixing (for example, in a conduit to the vessel), to provide a common flash vapor stream, or common flash vapor and vapor effluent stream, with associated common flash liquid stream.

The amount and composition of vapor and liquid that may be formed upon cooling or flashing various streams in the method of the present invention may vary widely. Such amounts and compositions of the phases are dependent upon the pressures and temperatures selected in conjunction with composition of the vapor product stream obtained from the oxygenate to olefin reaction. For example, higher pressures and lower temperatures tend to increase the amount of liquid obtained from cooling or exposing at any given composition of the vapor product stream. Further, a higher average molecular weight product slate in the vapor product stream, for example one having a relatively high amount of propylene and butylenes and a relatively low amount of methane and ethylene, will tend to increase the amount of vapor obtained from cooling or exposing at any given temperature or pressure.

Conveniently, when cooling or flashing a single stream or combination of streams to form a liquid effluent stream that is to be separated from a vapor effluent stream, the proportion of liquid effluent stream obtained is at least 1 wt. %, more particularly at least 5 wt. %, for example at least 10 wt. %, such as at least 20 wt. % of the total material in the stream so.cooled or exposed, and is no greater than 90 wt. %, more specifically no greater than 70 wt. %, by example no greater than 60 wt. %, such as no greater than 40 wt. % of the total material in the stream so cooled or exposed. In general, the lower the pressure and the higher the temperature at which the material in the stream is cooled or flashed, the lower the proportion of liquid formed, and vice versa.

Referring to FIG. 1, there is illustrated therein a process for converting methanol to olefins, particularly $C_2$ to $C_4$ olefins, according to one example of the invention. An oxygenate feedstock, for example, methanol, is provided in line 10 to oxygenate to olefin reactor 12 for conversion to a vapor product stream comprising $C_2$ to $C_4$ olefins, $C_2$ to $C_6$ carbonyl compounds and water, which exits the oxygenate to olefin reactor 12 in line 14 at a reaction pressure.

The vapor product stream in line 14 is provided to a cooling device, in this instance a quench tower 16. The cooling in quench tower 16 serves to condense a liquid water-rich bottoms stream in line 20 from the vapor product stream in line 14 near bottom of quench tower 16, and also provide, from near the top of quench tower 16, a first vapor effluent stream in line 18 at an initial pressure that is no greater than the reaction pressure, and further that comprises no more than 10 wt. % water. The first vapor effluent stream in line 18 is combined with a first wash flash vapor stream in line 42 to produce a common stream in line 22 that is provided to the suction of a compressor 24 at a first suction pressure that is no greater than the initial pressure.

The common stream in line 22 is compressed in compressor 24 to produce a second vapor effluent stream in line 26 that is at a second pressure greater than the first suction pressure. The second vapor effluent stream in line 26 is then cooled in cooling device, in this instance a shell and tube heat exchanger 28 with the entrance and exit of a cooling fluid denoted by the unnumbered lines. The cooling of the second effluent stream in line 26 through heat exchanger 28 serves to produce a cooled second effluent stream in line 30 that is at least partially in the vapor state.

The cooled second effluent stream is communicated via line 30 to a vapor-liquid contacting device, in this case absorber fractionation tower 32, at a point near the bottom of the absorber tower 32 to allow the vapor portion of the cooled second effluent stream to rise through the contacting device. An alcohol wash is effected at a third pressure in absorber tower 32 by providing a liquid alcohol-containing stream in line 34 to a point near the top of the absorber tower 32. Conveniently, the third pressure represents the highest pressure found within the vapor-liquid contacting device, in this case likely near the bottom of absorber tower 32, and is greater than the first suction pressure but no greater than the second pressure.

The liquid alcohol-containing stream in line 34 will flow down through the absorber tower 32, contacting the cooled second effluent stream, preferentially absorbing $C_2$ to $C_6$ carbonyl compounds, but also absorbing some $C_2$ and $C_3$ olefins and other hydrocarbons, thus producing a wash liquid stream in line 38 from near the bottoms of absorber tower 32. From near the top of absorber tower 32, a wash vapor stream is produced in line 36 that has a lower content of $C_2$ to $C_6$ carbonyl compounds than the first vapor effluent stream in line 18, suitable for further processing to recover and purify the various olefins. It is likely that the wash vapor stream in line 36 will further comprise some of the alcohol contained in the liquid alcohol-containing stream in line 34.

The wash liquid stream in line 38 is exposed to a pressure of at least the first suction pressure and less than the third pressure. The exposure, in this instance conducted in flash drum 40, will produce a first wash flash vapor stream in line 42 exiting near the top of flash drum 40, that as noted earlier is provided to the suction of compressor 24. The first wash flash vapor in line 42 will preferentially comprise the $C_2$ and $C_3$ olefins found in the wash liquid stream in line 38, and those $C_2$ and $C_3$ olefins will, conveniently, eventually be recovered in the wash vapor stream in line 36. The first wash flash vapor in line 42 may also comprise a relatively low proportion of the $C_2$ to $C_6$ carbonyl compounds found in the wash liquid stream in line 38, and those carbonyls would again be washed out in absorber tower 32 and appear in the wash liquid in line 38.

The exposure in the flash drum 40 also produces a first wash flash liquid stream in line 44 exiting near the bottom of flash drum 40. The first wash flash liquid in line 44 will preferentially comprise the $C_2$ to $C_6$ carbonyl compounds and the alcohol found in the wash liquid stream in line 38. Conveniently, sufficient $C_2$ to $C_6$ carbonyl compounds found in the first vapor effluent stream in line 18 will exit in the wash flash liquid in line 44, providing a wash vapor in line 36 that has a lower content of $C_2$ to $C_6$ carbonyl compounds than the first vapor effluent stream in line 18. The first wash flash liquid in line 44 may also comprise a relatively low proportion of the $C_2$ and $C_3$ olefins found in the wash liquid stream in line 38, and may be discarded or further processed, for example, provided to a water-oxygenate fractionation tower for recovery of the alcohol in the wash liquid stream in line 38 for use as oxygenate feedstock in line 10 for the oxygenate to olefins reactor 12.

Figure 2:
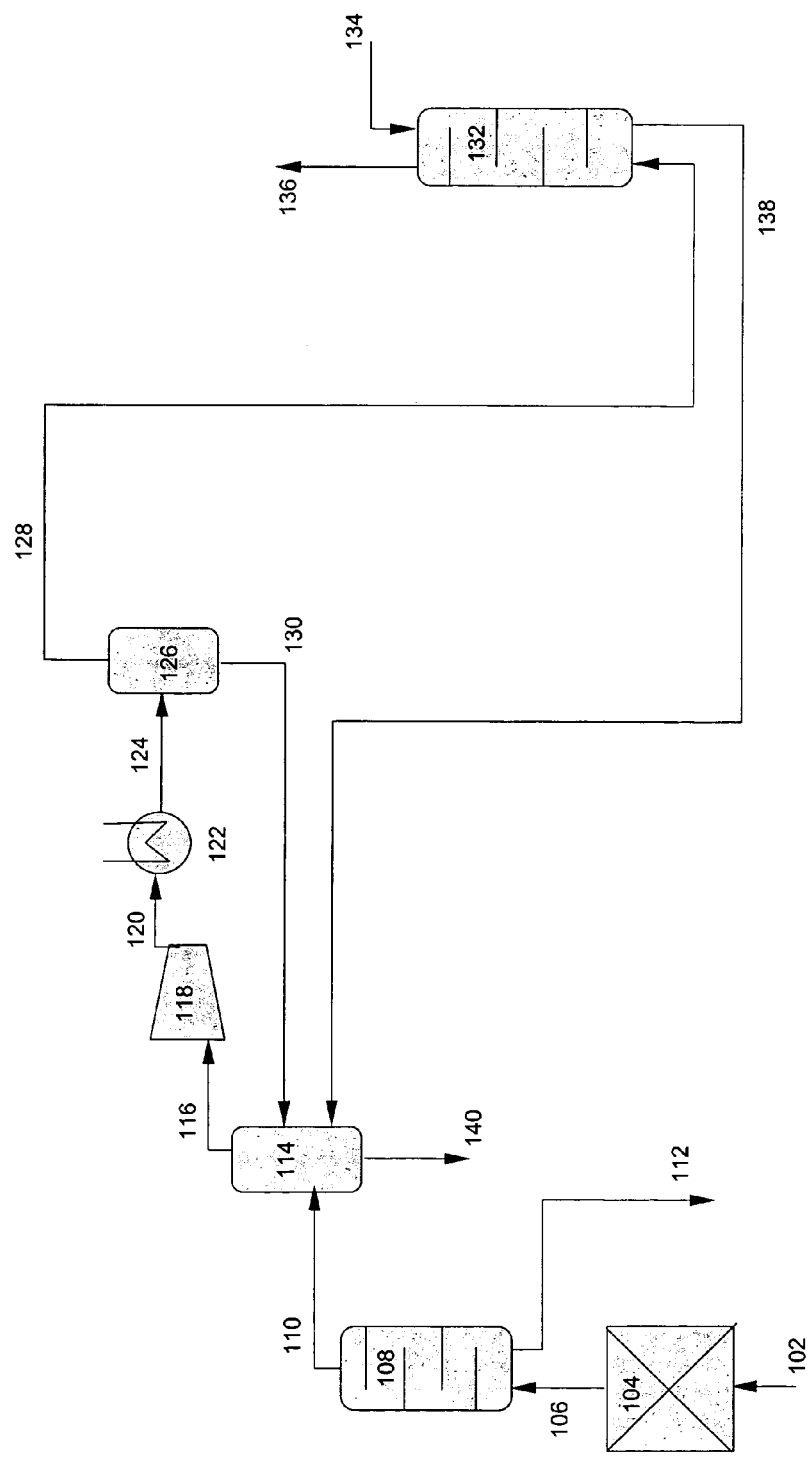
FIG. 2 is a schematic flow diagram illustrating a process according to another example of the invention.

Now turning attention to FIG. 2, there is illustrated therein a process for converting methanol to olefins, particularly $C_2$ to $C_4$ olefins, according to another example of the invention. An oxygenate feedstock, for example, methanol, is provided in line 102 to oxygenate to olefin reactor 104 for conversion to a vapor product stream comprising $C_2$ to $C_4$ olefins, $C_2$ to $C_6$ carbonyl compounds and water, which exits the oxygenate to olefin reactor 104 in line 106 at a reaction pressure.

The vapor product stream in line 106 is fed to a cooling device, in this instance a quench tower 108. The cooling in quench tower 108 serves to condense from the vapor product stream a liquid water-rich bottoms stream in line 112 near bottom of quench tower 108, and also provide, from near the top of quench tower 108, a first vapor effluent stream in line 110 at an initial pressure that is no greater than the reaction pressure, and further that comprises no more than 10 wt. % water. The first vapor effluent stream in line 110 is communicated, via flash drum 114 and line 116, to the suction of a compressor 118 at a first suction pressure that is no greater than the initial pressure.

The first vapor effluent stream is compressed in compressor 118 to produce a second vapor effluent stream in line 120 that is at a second pressure greater than the first suction pressure. The second vapor effluent stream in line 120 is then cooled in cooling device, in this instance a shell and tube heat exchanger 122. The cooling of the second effluent stream in line 120 through heat exchanger 122 serves to produce a cooled second effluent stream in line 124 that is at least partially in the vapor state. The cooled second effluent stream in line 124 is communicated to another flash drum 126 to form a cooled second vapor effluent stream in line 128 from near the top of flash drum 126, and the second liquid effluent stream in line 130.

The cooled second vapor effluent stream is communicated via line 128 to a vapor-liquid contacting device, in this case absorber fractionation tower 132, at a point near the bottom of the absorber tower 132. An alcohol wash is effected at a third pressure, greater than the first suction pressure but not greater than the second pressure, in absorber tower 132 by providing a liquid alcohol-containing stream in line 134 to a point near the top of the absorber tower 132. Segregating the cooled second vapor effluent in line 128 from the second liquid effluent in line 130 can prevent potential operating problems or design complexity in the vapor-liquid contacting device, by avoiding certain composition regimes in the vapor-liquid contacting device in which two liquid phases may form.

The liquid alcohol-containing stream in line 134 flows down through the absorber tower 132, contacting the cooled second vapor effluent stream, preferentially absorbing $C_2$ to $C_6$ carbonyl compounds, but also absorbing some $C_2$ and $C_3$ olefins and other hydrocarbons, thus producing a wash liquid stream in line 138 from near the bottoms of absorber tower 132. From near the top of absorber tower 132, a wash vapor stream is produced in line 136 that has a lower content of $C_2$ to $C_6$ carbonyl compounds than the first vapor effluent stream in line 110, suitable for further processing to recover and purify the various olefins. It is likely that the wash vapor stream in line 136 will further comprise some of the alcohol contained in the liquid alcohol-containing stream in line 134.

The wash liquid stream in line 138 is fed to the flash drum 114 along with the first vapor effluent stream in line 110, where the wash liquid stream is exposed to a pressure of at least the first suction pressure and less than the third pressure. The exposure produces a first wash liquid stream which exits the drum 114 through line 140 and a first wash flash vapor stream which flow from the drum 114 through line 116, as a common stream with the first vapor effluent stream, to the suction of compressor 118. Further, the second liquid effluent stream in line 130 is also directed to flash drum 114 for exposure to a pressure of at least the first suction pressure and less than the third pressure, in this instance the same pressure provided for the exposure of the wash liquid stream in line 138. Thus, a second wash flash vapor stream is also provided in line 116, as a common stream with the first vapor effluent stream and the first wash flash vapor stream 116, to the suction of compressor 118. Flashing the second effluent liquid stream in line 130 in flash drum 114 allows recovery of the $C_2$ and $C_3$ olefins in the second effluent liquid stream in line 130 into the suction of compressor 118, whereby the olefins can eventually be recovered in the wash vapor stream in line 136.

Figure 3:
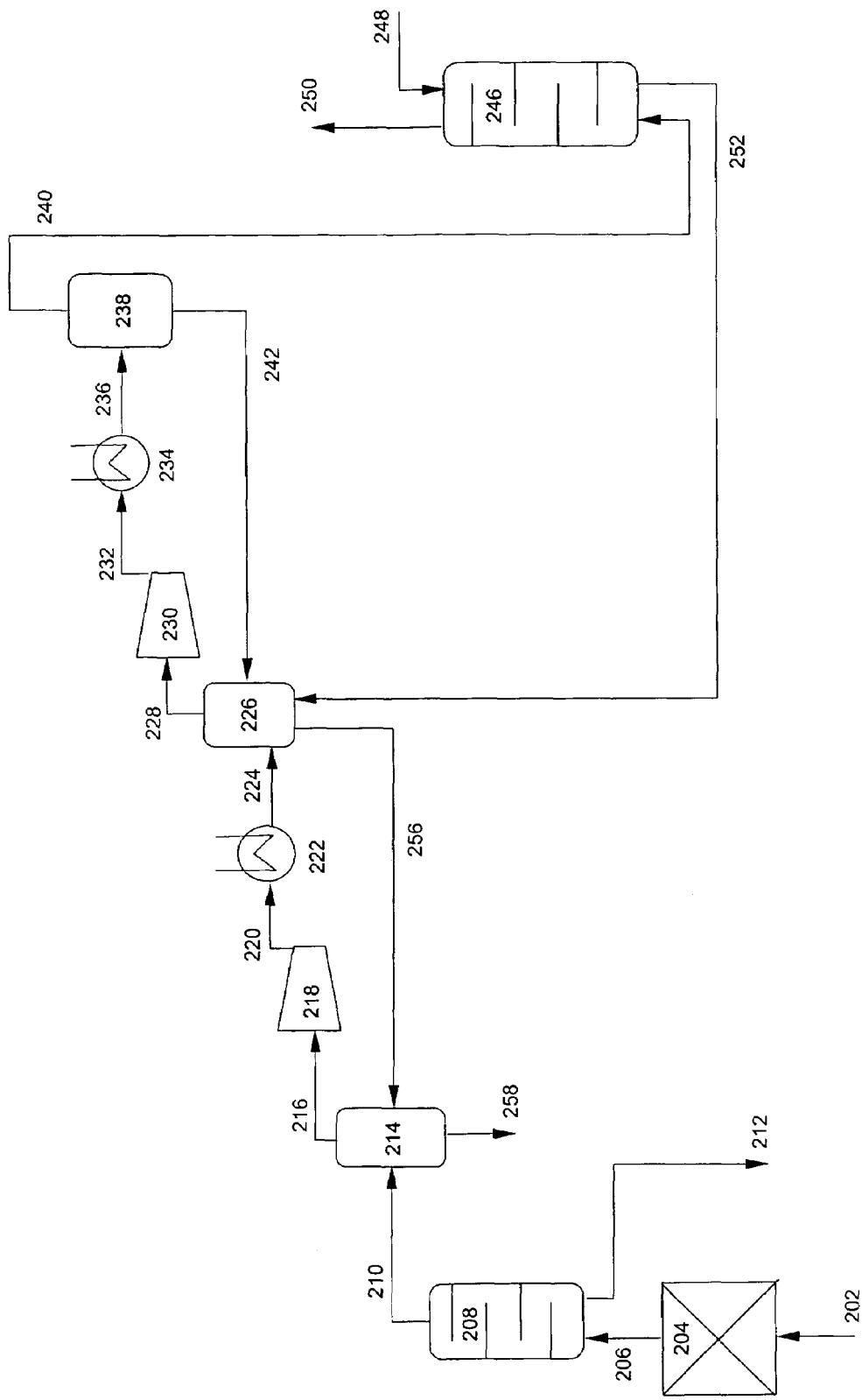
FIG. 3 is a schematic flow diagram illustrating a process according to yet another example of the invention.

Finally, with respect to FIG. 3, there is illustrated therein a process for converting methanol to olefins, particularly $C_2$ to $C_4$ olefins, according to yet another example of the invention. An oxygenate feedstock, for example, methanol, is provided in line 202 to oxygenate to olefin reactor 204 for conversion to a vapor product stream comprising $C_2$ to $C_4$ olefins, $C_2$ to $C_6$ carbonyl compounds and water, which exits the oxygenate to olefin reactor 204 in line 206 at a reaction pressure.

The vapor product stream in line 206 is provided to a cooling device, in this instance a quench tower 208. The cooling in quench tower 208 serves to condense a liquid water-rich bottoms stream in line 212 from the vapor product stream in line 202 near bottom of quench tower 208, and also provide, from near the top of quench tower 208, a first vapor effluent stream in line 210 at an initial pressure that is no greater than the reaction pressure, and further that comprises no more than 10 wt. % water. The first vapor effluent stream in line 210 is communicated, via a first flash drum 214, and line 216, to the suction of a compressor 218 at a first suction pressure that is no greater than the initial pressure.

The flash drum 214 also receives an intermediate effluent liquid stream through line 256 and exposes the intermediate effluent liquid stream to a pressure of at least the first suction pressure and less than an intermediate pressure to produce an intermediate flash vapor effluent stream and an intermediate flash liquid effluent stream. The intermediate flash vapor effluent stream exits the drum 214 through line 216, as a common stream with the first vapor effluent stream in line 216 (such common stream optionally termed a flash vapor added first effluent stream in line 216), to the suction of compressor 218. The intermediate flash liquid stream exits the drum 214 through line 258 and carries with it at least part of the $C_2$ to $C_6$ carbonyl compounds from the first vapor effluent stream in line 210.

The common first vapor effluent stream and intermediate flash vapor stream in line 216 is compressed in compressor 218 to produce an intermediate effluent stream in line 220 that is at an intermediate pressure greater than the initial pressure. The intermediate effluent stream in line 220 is then cooled in a cooling device, in this instance a shell and tube heat exchanger 222. The cooling of the intermediate effluent stream in line 220 through heat exchanger 222 serves to produce a cooled intermediate effluent stream in line 224 that is at least partially in the vapor state. The cooled intermediate effluent stream in line 224 is communicated to a second flash drum 226, which serves to produce an intermediate effluent vapor stream in line 228 and the intermediate effluent liquid stream in line 256. The intermediate effluent vapor stream in line 228 is communicated to the suction of another compressor 230 at an intermediate suction pressure that is no greater than the intermediate pressure.

The flash drum 226 also receives a second liquid effluent stream through line 242 and a wash liquid stream through line 252. In the flash drum 226, the second liquid effluent stream and the wash liquid stream are exposed to a pressure of at least the intermediate suction pressure and less than the third pressure to produce first and second wash flash vapor streams and first and second wash flash liquid streams. The first and second wash flash vapor streams exit the drum 226 through line 228, as a common stream with the intermediate effluent vapor stream, to the suction of compressor 230. Further, the first and second wash flash liquid streams exit the drum 226 through line 256, as a common stream with the intermediate effluent liquid stream and are returned to the first flash drum 214.

The first wash flash vapor stream along with the second wash flash vapor stream, as a common stream with the intermediate effluent vapor stream in line 228 is compressed in compressor 230 to produce a second vapor effluent stream in line 232 that is at a second pressure greater than the intermediate pressure. The second vapor effluent stream in line 232 is then cooled in cooling device, in this example another shell and tube heat exchanger 234. The cooling of the second effluent stream in line 232 through heat exchanger 234 serves to produce a cooled second effluent stream in line 236 that is at least partially in the vapor state. The cooled second effluent stream in line 236 is communicated to a third flash drum 238, to form a cooled second vapor effluent stream in line 240 from near the top of flash drum 238, and the second liquid effluent stream in line 242.

The cooled second vapor effluent stream is communicated via line 240 to a vapor-liquid contacting device, in this case absorber fractionation tower 246, at a point near the bottom of the absorber tower 246. An alcohol wash is effected at a third pressure, greater than the first suction pressure but not greater than the second pressure, in absorber tower 246 by providing a liquid alcohol-containing stream in line 248 at a point near the top of the absorber tower 246. The liquid alcohol-containing stream in line 248 flows down through the absorber tower 246, contacting the cooled second vapor effluent stream, preferentially absorbing $C_2$ to $C_6$ carbonyl compounds, but also absorbing some $C_2$ and $C_3$ olefins and other hydrocarbons, thus producing the wash liquid stream in line 252 from near the bottoms of absorber tower 246. From near the top of absorber tower 246, a wash vapor stream is produced in line 250 that has a lower content of $C_2$ to $C_6$ carbonyl compounds than the first vapor effluent stream in line 210, suitable for further processing to recover and purify the various olefins. It is likely that the wash vapor stream in line 250 will further comprise some of the alcohol contained in the liquid alcohol-containing stream in line 248.

In an optional embodiment, the wash vapor stream is then subjected to a second washing step in which the wash vapor stream is washed with water in a second vapor-liquid contacting device, again typically a countercurrent fractional distillation tower, to produce a water-washed vapor stream as an overhead product and an liquid oxygenate-containing water stream as a bottoms product. Conveniently, the liquid water employed in the second washing step is the substantially pure water bottoms stream obtained from the water-oxygenate fractionation tower.

In general, the temperature employed in the second washing step should be no more than 120° F. (49° C.) so as to enhance the oxygenate adsorption capacity of the water and limit the amount of water vapor exiting the second vapor-liquid contacting device with the water-washed vapor stream. Conveniently, the temperature of the second washing step is at least 70° F. (21° C.), for example at least 80° F. (27° C.), such as at least 90° F., and no more than 110° F. (43° C.), for example no more than 100° F. (38° C.). Conveniently, the second washing step is conducted at a pressure in the same ranges as noted earlier for the third pressure, and in a specific embodiment slightly below (say about 5 to about 20 psi below) said third pressure.

Conveniently, said water-washed vapor stream comprises less than 0.5 wt. %, such as less than 0.1 wt %, for example less than 500 ppmwt, of $C_2$ to $C_6$ carbonyl compounds. In addition, the water-washed vapor stream conveniently comprises less than 1.0 wt. %, such as less than 0.1 wt %, for example less than 500 ppmwt, of methanol. The water-washed vapor stream can then be processed to recover the $C_2$ to $C_4$ olefins and higher hydrocarbons present in this stream.

In one embodiment of such a recovery process, at least part of the water-washed vapor stream is contacted with a basic component, such as caustic or an amine, to remove the bulk of the carbon dioxide therefrom (thus removing "acid gas" from the water-washed vapor stream), whereafter the $CO_2$-depleted stream is dried, for example in a molecular sieve drier, so that the dried effluent stream has a dew point no greater than −150° F. (−101° C.), such as no greater than −200° F. (−129° C.).

In another embodiment of such a recovery process, at least part of the $C_3$ and $C_4$ hydrocarbons contained in the fourth vapor effluent stream, or in the dried fourth effluent stream, is separated to produce a $C_3$ containing stream and a first $C_4$ containing stream. This separation is effected, for example, in a fractional distillation tower, wherein the $C_3$ containing stream is taken as an overhead product and the first $C_4$ containing stream is taken as a bottoms product. This separation may be conducted either before or after separating $C_2$− hydrocarbons from the fourth vapor effluent stream, and the $C_3$ and $C_2$− hydrocarbons can be further processed to produce high purity, e.g., 95 wt. % or greater, such as 99 wt. % or greater, ethylene and propylene, in other separation steps such as fractional distillation columns.

The composition of the first $C_4$ containing stream can vary widely, depending, for example, on the sequence of separation steps to which the fourth vapor effluent stream or dried fourth effluent stream is conducted, e.g., the order in which fractional distillation of various components is conducted. In one embodiment, the first vapor effluent stream comprises $C_5+$ hydrocarbons, and at least part of the $C_3$ and $C_4$ hydrocarbons contained in the fourth vapor effluent stream, or in the dried fourth effluent stream, is separated to produce a $C_3$ containing stream and a first $C_4$ containing stream prior to separation of $C_4$ hydrocarbons from $C_5+$ hydrocarbons. In this embodiment, the separation is conducted such that there is a low amount of dimethyl ether in the first $C_4$ containing stream, generally 1 wt. % or less, such as 0.5 wt. % or less, or 0.1 wt. % or less, or even 500 wppm or less.

In this embodiment, the first $C_4$ containing stream comprises at least 40 wt %, such as at least 50 wt %, such as at least 60 wt % of $C_4$ hydrocarbons, including $C_4$ olefins, and at least 10 wt %, such as at least 15 wt %, for example at least 20 wt %, of $C_5$ hydrocarbons, including $C_5$ olefins, and varying amounts of $C_6$ and higher hydrocarbons. Typically the first $C_4$ containing stream comprises less than 5 wt %, such as less than 1 wt %, for example less than 0.1 wt % $C_3$ and lower hydrocarbons and no more than 5 wt %, such as no more than 2 wt %, such as no more than 1 wt %, such as no more than 5000 ppm wt, such as no more than 1000 ppm wt, such as no more than 500 ppm wt, for example no more than 250 ppm wt, of $C_2$ to $C_6$ carbonyl compounds. The first $C_4$ containing stream can be extracted directly as a product stream for use as a fuiel gas or as a feed for processes, such as, hydrogenation (for example, to convert butadiene to butenes and butane), alkylation (for example, to produce higher saturated hydrocarbons), and oligomerization (for example, to produce higher olefins). Alternatively, the first $C_4$ containing stream can undergo further separation into its individual components.

The invention will now be more particularly described with reference to the following practical example of the process shown in FIG. 1.

EXAMPLE pilot plant trial of the process shown in FIG. 1 was conducted in which the second effluent stream was washed in the absorber fractionation tower 32 at a pressure of 150 psig (1135 kPa) and a methanol flow rate of 15 lb/hour. The composition of the second vapor effluent stream in line 26 and the wash vapor stream in line 36 are shown below in Table 1.

TABLE 1

| Component | Second Effluent Stream (wt %) | Wash Vapor Stream (wt %) | % Change |
|---|---|---|---|
| Dimethyl ether | 3.7661 | 2.7718 | −26.4015 |
| Methyl ethyl ether | 0.0101 | 0.0000 | −100.0000 |
| Methyl isopropyl ether | 0.0007 | 0.0000 | −100.0000 |
| Acetaldehyde | 0.0417 | 0.0378 | −9.5362 |
| 2-Methoxy butane | 0.0002 | 0.0000 | −100.0000 |
| Propanal | 0.0111 | 0.0000 | −100.0000 |
| Acrolein | 0.0001 | 0.0000 | −100.0000 |
| Methacrolein | 0.0036 | 0.0000 | −100.0000 |
| Unknown | 0.0003 | 0.0000 | −100.0000 |
| Butanal | 0.0032 | 0.0000 | −100.0000 |
| Methyl acetate | 0.0002 | 0.0000 | −100.0000 |
| Methanol | 2.7353 | 2.3179 | −15.2629 |
| Acetone | 0.1601 | 0.0813 | −49.2466 |
| Isovaleraldehyde | 0.0003 | 0.0000 | −100.0000 |
| Dimethylacetal | 0.0020 | 0.0000 | −100.0000 |
| Pentanal | 0.0005 | 0.0000 | −100.0000 |
| 2-Butanone | 0.0375 | 0.0000 | −100.0000 |
| Ethanol | 0.0008 | 0.0000 | −100.0000 |
| 3-Methyl-3-buten-2-one | 0.0014 | 0.0000 | −100.0000 |
| Unknown | 0.0002 | 0.0000 | −100.0000 |
| Crotonaldehyde | 0.0002 | 0.0000 | −100.0000 |
| 3-Methyl-2-butanone | 0.0042 | 0.0000 | −100.0000 |
| 3-Pentanone | 0.0021 | 0.0000 | −100.0000 |
| 2-Methyl butanol | 0.0002 | 0.0000 | −100.0000 |
| 2-Pentanone | 0.0022 | 0.0000 | −100.0000 |
| 3-Butenol | 0.0003 | 0.0000 | −100.0000 |
| 3-Methyl-2-pentanone | 0.0003 | 0.0514 | 19009.5609 |
| t-Butanol | 0.0001 | 0.0000 | −100.0000 |
| Methane | 1.2653 | 1.2563 | 0.0000 |
| Ethane | 0.5437 | 0.5308 | −2.3655 |
| Ethylene | 30.6933 | 29.9435 | −2.4430 |
| Propane | 0.9249 | 0.7663 | −17.1554 |
| Cyclopropane | 0.0031 | 0.0000 | −100.0000 |
| Propylene | 35.4988 | 31.0685 | −12.4804 |
| Isobutane | 0.0849 | 0.0587 | −30.8560 |
| n-Butane | 0.2579 | 0.1672 | −35.1748 |
| Methyl cyclopropane | 0.0039 | 0.0000 | −100.0000 |
| Trans-2-Butene | 5.1322 | 3.6158 | −29.5467 |
| 1-Butene | 3.3856 | 2.5235 | −25.4634 |
| Iso-Butene | 0.7129 | 0.5469 | −23.2929 |
| Cis-2-Butene | 3.8081 | 2.6364 | −30.7689 |
| Isopentane | 0.0043 | 0.0349 | 706.3496 |
| 1,2-Butadiene | 0.0561 | 0.0000 | −100.0000 |
| Pentane | 0.0581 | 0.0000 | −100.0000 |
| Methyl acetylene | 0.0022 | 0.0000 | −100.0000 |
| 1,3-Butadiene | 0.4457 | 0.0280 | −93.7131 |
| C5+ | 10.3408 | 4.0294 | −61.0339 |
| H2O/CO/CO2 | 0.0000 | 0.1403 | Undefined | will be seen from Table 1 that the methanol wash removes all the oxygenates in the second vapor effluent stream, except for part of the dimethyl ether, acetaldehyde, acetone and 3-methyl-pentanone. However, it will be seen that the methanol wash step also removes non-negligible amounts of ethylene and propylene product. In order to prevent these losses, the wash liquid stream in line 38 is fed to the flash drum 40 so that the olefin products can be vaporized into the first wash flash vapor and fed back in line 42 to the compressor 24.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing olefins comprising:
   (a) providing a vapor product stream from an oxygenate to olefin reaction, said vapor product stream comprising $C_2$ to $C_4$ olefins, $C_2$ to $C_6$ carbonyl compounds and water;
   (b) cooling said vapor product stream to provide a first vapor effluent stream comprising no more than 10 wt. % water, and a liquid water-rich stream;
   (c) compressing the first vapor effluent stream and a first wash flash vapor stream from a first suction pressure to a second pressure greater than said first pressure to form a second vapor effluent stream;
   (d) cooling the second vapor effluent stream to form a cooled second effluent stream that is at least partially in the vapor state;
   (e) washing at least part of the cooled second effluent stream with a liquid alcohol-containing stream, at a third pressure greater than the first suction pressure but not greater than the second pressure, to produce a wash liquid stream comprising $C_3$ and $C_4$ olefins, and a wash vapor stream, said wash vapor stream having a lower content of $C_2$ to $C_6$ carbonyl compounds than the first vapor effluent stream; and
   (f) exposing the wash liquid stream to a pressure of at least the first suction pressure but less than the third pressure to form a first wash flash liquid stream and said first wash flash vapor stream, said first wash flash vapor stream being provided for compression (c).

2. The process of claim 1 wherein said cooling (b) is conducted in an indirect heat exchanger or in a direct contact quenching device.

3. The process of claim 1 wherein said cooling (b) is conducted in a direct contact quenching device.

4. The process of claim 1 wherein the first vapor effluent stream comprises from about 0.5 to about 5 wt % of said carbonyl compounds.

5. The process of claim 1 wherein the first vapor effluent stream comprises from about 1 to about 4 wt % of said carbonyl compounds.

6. The process of claim 1 wherein the first vapor effluent stream comprises no more than 5 wt % water.

7. The process of claim 1 wherein the first vapor effluent stream comprises no more than 2 wt % water.

8. The process of claim 1 wherein said first vapor effluent stream produced in (b) is at an initial pressure of from about 1 psig to about 100 psig (108 to 790 kPa).

9. The process of claim 1 wherein said first vapor effluent stream produced in (b) is at an initial pressure of from about 5 psig to about 80 psig (135 to 653 kPa).

10. The process of claim 1 wherein said first suction pressure is no more than 40 psi (275 kPa) below the pressure of said first vapor effluent stream produced in (b).

11. The process of claim 1 wherein said first suction pressure is no more than 10 psi (69 kPa) below the pressure of said first vapor effluent stream produced in (b).

12. The process of claim 1 wherein the temperature of the first vapor effluent stream is about 70° F. (21° C.) to about 120° F. (49° C.).

13. The process of claim 1 wherein the temperature of the first vapor effluent stream is about 80° F. (27° C.) to about 110° F. (43° C.).

14. The process of claim 1 wherein said second pressure is at least 50 psig (445 kPa) and no greater than 350 psig (2514 kPa).

15. The process of claim 1 wherein said second pressure is at least 100 psig (790 kPa) and no greater than 200 psig (1480 kPa).

16. The process of claim 1 wherein said cooling (d) produces said cooled second effluent stream with a temperature of about 70° F. (21° C.) to about 120° F. (49° C.).

17. The process of claim 1 wherein said cooling (d) produces said cooled second effluent stream with a temperature of about 80° F. (27° C.) to about 110° F. (43° C.).

18. The process of claim 1 wherein said liquid alcohol-containing stream used in said washing (e) comprises methanol.

19. The process of claim 1 wherein the temperature in said washing (e) is about 80° F. (27° C.) to about 120° F. (49° C.).

20. The process of claim 1 wherein the temperature in said washing (e) is about 90° F. to about 110° F. (43° C.).

21. The process of claim 1 wherein said third pressure is at least 50 psig (445 kPa) and no greater than 350 psig (2514 kPa).

22. The process of claim 1 wherein said third pressure is at least 100 psig (790 kPa) and no greater than 200 psig (1480 kPa).

23. The process of claim 1 wherein said wash liquid stream comprises at least 1 wt. % $C_3$ and $C_4$ olefins.

24. The process of claim 1 wherein said wash liquid stream comprises at least 5 wt. % $C_3$ and $C_4$ olefins.

25. The process of claim 1 wherein said wash liquid stream comprises at least 10 wt. % $C_3$ and $C_4$ olefins.

26. The process of claim 1 wherein said wash liquid stream comprises at least 20 wt. % $C_3$ and $C_4$ olefins.

27. The process of claim 1 wherein said wash liquid stream comprises no greater than 50 wt. % $C_3$ and $C_4$ olefins.

28. The process of claim 1 wherein said wash liquid stream comprises at least 1 wt. % and no greater than 50 wt. % $C_3$ and $C_4$ olefins.

29. The process of claim 1 wherein said vapor product stream in (a) further comprises $C_5$ olefins, and said wash liquid stream further comprises $C_5$ olefins.

30. The process of claim 29 wherein said wash liquid stream comprises at least 1 wt. % $C_3$ to $C_5$ olefins.

31. The process of claim 29 wherein said wash liquid stream comprises at least 1 wt. % and no greater than 60 wt. % $C_3$ to $C_5$ olefins.

32. The process of claim 1 wherein the pressure employed in the exposing (f) is from about 1 psig to about 100 psig (108 to 790 kPa).

33. The process of claim 1 wherein the pressure employed in the exposing (f) is from about 5 psig to about 80 psig (135 to 653 kPa).

34. The process of claim 1 wherein the temperature employed in the exposing (f) is about 40° F. (4° C.) to about 120° F. (49° C.).

35. The process of claim 1 wherein the temperature employed in the exposing (f) is about 60° F. (16° C.) to about 110° F. (43° C.).

36. The process of claim 1 wherein the cooling (d) produces a cooled second vapor effluent stream and a second liquid effluent stream, said cooled second vapor effluent stream vapor being washed in (e), and said second liquid effluent stream being exposed to a pressure of at least the first suction pressure and no greater than the third pressure to form a second wash flash liquid stream and a second wash flash vapor stream, said second wash flash vapor stream also being provided for compression (c).

37. The process of claim 36 wherein the exposing (f) occurs in a vessel, and the second liquid effluent stream is also introduced to said vessel to provide the first and second wash flash vapor streams as a common stream for compression (c), and the first and second wash flash liquid streams as a common stream.

38. The process of claim 37 wherein the second liquid effluent stream is combined with the wash liquid stream prior to being introduced to said vessel.

39. The process of claim 37 wherein the first vapor effluent stream is also introduced to the vessel used in (f), whereby the first vapor effluent stream, and the first and second wash flash vapor streams are provided as a common stream for compression (c).

40. The process of claim 1 wherein the cooling (b) and exposing (f) are effected in the same device to provide the first vapor effluent stream and first wash flash vapor stream as a common stream for compression (c), and the liquid water-rich stream and first wash flash liquid stream as a common stream.

41. The process of claim 36 wherein the cooling (b) and exposing (f) are effected in the same device, and the second liquid effluent stream is also provided to said device, to provide the first effluent stream, the first wash flash vapor stream and the second wash flash vapor stream as a combined stream for compression (c) and the liquid water-rich stream and first wash flash liquid stream and the second wash flash liquid stream as a common stream.

42. The process of claim 41 wherein the second liquid effluent stream is combined with the wash liquid stream prior to being provided to said device.

43. A process for producing olefins comprising:
(a) providing a vapor product stream from an oxygenate to olefin reaction, said product comprising $C_2$ to $C_4$ olefins, $C_2$ to $C_6$ carbonyl compounds and water;
(b) cooling said vapor product stream to provide a first vapor effluent stream at a first pressure and comprising no more than 10 wt. % water, and a liquid water-rich stream;
(c) compressing the first vapor effluent stream from a first suction pressure that is no greater than said first pressure to an intermediate pressure greater than said first pressure to form an intermediate effluent stream;
(d) cooling the intermediate effluent stream to form an intermediate effluent vapor stream and an intermediate effluent liquid stream;
(e) compressing the intermediate effluent vapor stream from an intermediate suction pressure that is no greater than said intermediate pressure to a second pressure greater than said intermediate pressure to form a second effluent stream;
(f) cooling the second effluent stream to form a cooled second effluent stream that is at least partially vapor;
(g) washing at least part of the cooled second effluent stream with a liquid alcohol-containing stream in a vapor-liquid contacting device, at a third pressure greater than the intermediate suction pressure but not greater than the second pressure, to produce a wash liquid stream comprising $C_3$ and $C_4$ olefins, and a wash vapor stream, said wash vapor stream having a lower content of $C_2$ to $C_6$ carbonyl compounds than the first vapor effluent stream; and
(h) exposing at least part of the wash liquid stream to a pressure of at least the first suction pressure and less than the third pressure to form a first wash flash liquid stream and a first wash flash vapor stream, said first wash flash vapor stream being provided for compression (c) along with the first vapor effluent stream, or for compression (e) along with the intermediate effluent vapor stream, or both.

44. The process of claim 43 wherein said cooling (b) is conducted in an indirect heat exchanger or in a direct contact quenching device.

45. The process of claim 43 wherein said cooling (b) is conducted in a direct contact quenching device.

46. The process of claim 43 wherein said first pressure is from about 1 psig to about 100 psig (108 to 790 kPa).

47. The process of claim 43 wherein said first pressure is from about 5 psig to about 80 psig (135 to 653 kPa).

48. The process of claim 43 wherein said first suction pressure is no more than 40 psi (275 kPa) below said first pressure.

49. The process of claim 43 wherein said first suction pressure is no more than 10 psi (69 kPa) below said first pressure.

50. The process of claim 43 wherein said intermediate pressure is greater than 5 psig (135 kPa) and less than 350 psig (2514 kPa).

51. The process of claim 43 wherein said intermediate pressure is greater than 40 psig (376 kPa) and less than 200 psig (1480 kPa).

52. The process of claim 43 wherein said intermediate suction pressure is no more than 30 psi (206 kPa) below said intermediate pressure.

53. The process of claim 43 wherein said intermediate suction pressure is no more than 10 psi (69 kPa) below said intermediate pressure.

54. The process of claim 43 wherein said second pressure is greater than 100 psig (790 kPa) and less than 350 psig (2514 kPa).

55. The process of claim 43 wherein said second pressure is greater than 140 psig (1066 kPa). and less than 200 psig (1480 kPa).

56. The process of claim 43 wherein said third pressure is greater than 100 psig (790 kPa) and less than 350 psig (2514 kPa).

57. The process of claim 43 wherein said third pressure is greater than 140 psig (1066 kPa). and less than 200 psig (1480 kPa).

58. The process of claim 43 wherein said wash liquid stream comprises at least 1 wt. % $C_3$ and $C_4$ olefins.

59. The process of claim 43 wherein said wash liquid stream comprises at least 5 wt. % $C_3$ and $C_4$ olefins.

60. The process of claim 43 wherein said wash liquid stream comprises at least 10 wt. % $C_3$ and $C_4$ olefins.

61. The process of claim 43 wherein said wash liquid stream comprises at least 20 wt. % $C_3$ and $C_4$ olefins.

62. The process of claim 43 wherein said wash liquid stream comprises no greater than 50 wt. % $C_3$ and $C_4$ olefins.

63. The process of claim 43 wherein said wash liquid stream comprises at least 1 wt. % and no greater than 50 wt. % $C_3$ and $C_4$ olefins.

64. The process of claim 43 wherein said vapor product stream in (a) further comprises $C_5$ olefins, and said wash liquid stream further comprises $C_5$ olefins.

65. The process of claim 64 wherein said wash liquid stream comprises at least 1 wt. % $C_3$ to $C_5$ olefins.

66. The process of claim 64 wherein said wash liquid stream comprises at least 1 wt. % and no greater than 60 wt. % $C_3$ to $C_5$ olefins.

67. The process of claim 43 wherein the pressure employed in the exposing (h) is from about 1 psig to about 350 psig (108 to 2514 kPa).

68. The process of claim 43 wherein the pressure employed in the exposing (h) is from about 5 psig to about 200 psig (135 to 1480 kPa).

69. The process of claim 43 wherein said intermediate effluent liquid stream is exposed to a pressure of at least the first suction pressure and less than the intermediate pressure to provide an intermediate flash vapor effluent stream and an intermediate flash liquid effluent stream, and said intermediate flash vapor effluent stream is provided for compression to a pressure no greater than said intermediate pressure.

70. The process of claim 69 wherein said intermediate flash vapor effluent stream is provided for compression (c) along with said first vapor product effluent stream.

71. The process of claim 70 wherein exposing of said intermediate effluent liquid stream occurs in a vessel, and said first vapor product stream is also introduced to said vessel to provide the intermediate flash vapor effluent stream and first vapor product stream as a common stream for compression (c).

72. The process of claim 43 wherein the cooling (f) produces a cooled second vapor effluent stream and a second liquid effluent stream, said cooled second vapor effluent stream being provided for washing (g), and said second liquid effluent stream being exposed to a pressure of at least the first suction pressure and no greater than the third pressure to form a second wash flash liquid stream and a second wash flash vapor stream, said second wash flash vapor stream also being provided for compression (c) along with the first effluent stream, or for compression (e) along with the intermediate effluent vapor stream, or both.

73. The process of claim 72 wherein said second liquid effluent stream is exposed to a pressure of at least the intermediate suction pressure and said second wash flash vapor stream is provided for compression (e) along with the intermediate effluent vapor stream.

74. The process of claim 72 wherein the cooled second effluent stream is introduced into a vessel to form the cooled second vapor effluent stream and the second liquid effluent stream.

75. The process of claim 43 wherein the wash liquid stream in (h) is exposed to a pressure of at least the intermediate suction pressure and said first wash flash vapor stream is provided for compression (e) along with the intermediate effluent vapor stream.

76. The process of claim 75 wherein exposing (h) occurs in a vessel, and the second liquid effluent stream is also introduced to said vessel to provide the first wash flash vapor stream and second wash flash vapor stream as a common stream for compression (c), or compression (e), or both, and to provide the first wash flash liquid and the second wash flash liquid as a common stream.

77. The process of claim 75 wherein the second liquid effluent stream is combined with said wash liquid stream prior to being introduced to said vessel.

78. The process of claim 75 wherein the cooled intermediate effluent stream from (d) is also introduced into the vessel to provide the first wash flash vapor stream and the second wash flash vapor stream and the intermediate effluent vapor stream as a common stream for compression (e), and the first wash flash liquid and the second wash flash liquid and the intermediate effluent liquid stream as a common stream.

79. The process of claim 78 wherein the cooled intermediate effluent stream from (d) is combined with the second liquid effluent stream and/or the wash liquid stream prior to being introduced into the vessel.

80. A process for producing olefins comprising:
(a) providing a vapor product stream from an oxygenate to olefin reaction, said product comprising $C_2$ to $C_4$ olefins, $C_2$ to $C_6$ carbonyl compounds and water;
(b) cooling said vapor product stream to provide a first vapor effluent stream at a first pressure and comprising no more than 10 wt. % water, and a liquid water-rich stream;
(c) introducing the first vapor effluent stream and an intermediate effluent liquid stream into a first vessel to form a flash vapor added first effluent stream and a first vessel liquid stream;
(d) compressing the flash vapor added first effluent stream to an intermediate pressure to form an intermediate effluent stream;
(e) cooling the intermediate effluent stream and introducing said cooled intermediate effluent stream into a second vessel together with a second liquid effluent stream and a wash liquid stream to form an intermediate effluent vapor stream and said intermediate effluent liquid stream;
(f) compressing the intermediate effluent vapor stream to a second pressure greater than said intermediate pressure to form a second effluent stream;
(g) cooling the second effluent stream and introducing said cooled second effluent stream into a third vessel to form a cooled second vapor effluent stream and said second liquid effluent stream; and
(h) washing the cooled second vapor effluent stream with an liquid alcohol-containing stream in a vapor-liquid contacting device, at a third pressure of greater than the intermediate pressure but no greater than the second pressure, to produce said wash liquid stream comprising $C_3$ and $C_4$ olefins, and a wash vapor stream, said wash vapor stream having a lower content of $C_2$ to $C_6$ carbonyl compounds than the first effluent stream.

81. The process of claim 80 wherein said cooling (b) is conducted in an indirect heat exchanger or in a direct contact quenching device.

82. The process of claim 80 wherein said cooling (b) is conducted in a direct contact quenching device.

83. The process of claim 80 wherein said first pressure is from about 1 psig to about 100 psig (108 to 790 kPa).

84. The process of claim 80 wherein said first vapor effluent stream and the intermediate effluent liquid stream are combined before being introduced into said first vessel in (c).

85. The process of claim 80 wherein said intermediate pressure is greater than 40 psig (376 kPa) and less than 350 psig (2514 kPa).

86. The process of claim 80 wherein said second pressure is greater than 100 psig (790 kPa) and less than 350 psig (2514 kPa).

87. The process of claim 80 wherein said third pressure is greater than 100 psig (790 kPa) and less than 350 psig (2514 kPa).

88. The process of claim 80 wherein said wash liquid stream comprises at least 1 wt. % $C_3$ and $C_4$ olefins.

89. The process of claim 80 wherein said wash liquid stream comprises at least 5 wt. % $C_3$ and $C_4$ olefins.

90. The process of claim 80 wherein said wash liquid stream comprises at least 10 wt. % $C_3$ and $C_4$ olefins.

91. The process of claim 80 wherein said wash liquid stream comprises at least 20 wt. % $C_3$ and $C_4$ olefins.

92. The process of claim 80 wherein said wash liquid stream comprises no greater than 50 wt. % $C_3$ and $C_4$ olefins.

93. The process of claim 80 wherein said wash liquid stream comprises at least 1 wt. % and no greater than 50 wt. % $C_3$ and $C_4$ olefins.

94. The process of claim 80 wherein said vapor product stream in (a) further comprises $C_5$ olefins, and said wash liquid stream further comprises $C_5$ olefins.

95. The process of claim 94 wherein said wash liquid stream comprises at least 1 wt. % $C_3$ to $C_5$ olefins.

96. The process of claim 94 wherein said wash liquid stream comprises at least 1 wt. % and no greater than 60 wt. % $C_3$ to $C_5$ olefins.

97. The process of claim 80 wherein the second liquid effluent stream is combined with said wash liquid stream prior to being introduced into said second vessel.

* * * * *